US008436022B2

(12) United States Patent
Kim et al.

(10) Patent No.: US 8,436,022 B2
(45) Date of Patent: *May 7, 2013

(54) BIARYL BENZOLMIDAZOLE DERIVATIVES AND PHARMACEUTICAL COMPOSITION COMPRISING THE SAME

(75) Inventors: Ji Duck Kim, Yongin-si (KR); Hong-Chul Yoon, Paju-si (KR); In Woo Kim, Seoul (KR); Hyae Jung Hyun, Yongin-si (KR)

(73) Assignee: Daewoong Pharmaceutical Co., Ltd., Seongnam-Si (KR)

( * ) Notice: Subject to any disclaimer, the term of this patent is extended or adjusted under 35 U.S.C. 154(b) by 884 days.

This patent is subject to a terminal disclaimer.

(21) Appl. No.: 12/373,193

(22) PCT Filed: Jul. 11, 2007

(86) PCT No.: PCT/KR2007/003362
§ 371 (c)(1),
(2), (4) Date: Jan. 9, 2009

(87) PCT Pub. No.: WO2008/007900
PCT Pub. Date: Jan. 17, 2008

(65) Prior Publication Data
US 2009/0209540 A1 Aug. 20, 2009

(30) Foreign Application Priority Data
Jul. 11, 2006 (KR) .................. 10-2006-0065115

(51) Int. Cl.
*A61K 31/4439* (2006.01)
*C07D 401/04* (2006.01)

(52) U.S. Cl.
USPC ......................................... 514/333; 546/256

(58) Field of Classification Search .................. 546/256; 514/333
See application file for complete search history.

(56) References Cited

U.S. PATENT DOCUMENTS

| 6,476,045 | B1 | 11/2002 | Dinnell et al. |
| 2002/0022624 | A1 | 2/2002 | Dinnell et al. |

FOREIGN PATENT DOCUMENTS

| JP | 2001-039034 | A | 2/2001 |
| JP | 2002-514635 | A | 5/2002 |
| JP | 2003-515560 | A | 5/2003 |
| JP | 2005-530760 | A | 10/2005 |
| JP | 2006-516626 | A | 7/2006 |
| WO | 99/58518 | A2 | 11/1999 |
| WO | 2006/080821 | A1 | 8/2006 |
| WO | 2007/034277 | A1 | 3/2007 |
| WO | 2007/059230 | A2 | 5/2007 |

OTHER PUBLICATIONS

Vippagunta et al., "Crystalline Solids", Advanced Drug Delivery Reviews 48 (2001) 3-26.*
Jain et al., "Polymorphism in Pharmacy", Indian Drugs, 1986, 23(6), 315-329.*
Guillory (in Brittain ed.), "Polymorphism in Pharmaceutical Sciences.," NY: Marcel Dekker, Inc., 1999, 1-2,125-181, 183-226.*
Wong et al. "Therapeutic potential, etc.," Brain Research Reviews 60 (2009) 267-277.*
Voight et al., Transient receptor, etc., Expert Opin. Ther. Patents (2010) 20(9) 1107-1122.*
Cortright et al., "Biochemical pharmacology, etc.," Eur. J. Biochem. 271, 1814-1819 (2004).*
Khairatkar-Joshi et al., "TRPV1 antagonists, etc." Trends in Molecular Medicine 15(1) 14-22.*
European Search Report issued in corresponding EP Application No. 07768695.4, dated Dec. 16, 2010.
Database Beilstein (Online), Beilstein Institute for Organic Chemistry (XP002611345, Database Accession No. 7081584, 7066799), J. Heterocycl. Chem., 1994, vol. 31, No. 4, pp. 957-966 (Abstract).
Database Beilstein (Online), Beilstein Institute for Organic Chemistry(XP002611346, Database Accession No. 8219673, 8220719), Synlett, 1999, vol. 3, pp. 307-310 (abstract).
Database Beilstein (Online), Beilstein Institute for Organic Chemistry (XP002611347, Database Accession No. 8642319, 8642539, 8656261, 8642346, 8642573), J. Med. Chem., 2000, vol. 43, pp. 1293-1310 (Abstract).
Appendino et al., "TRPV1 (Vanilloid Receptor, Capsaicin Receptor) Agonists and Antagonists," Expert Opin. Ther. Patents, 2003, vol. 13, No. 12, pp. 1825-1837.
Blettner et al., "Parallel Synthesis of Polyethylene Glycol Supported Biaryl Benzimadizoles and Imidazopyridines," Synlett, 1999, No. 3, pp. 307-310.
Dubey et al., "Synthesis of 1-alkyl-2-(substituted-2-pyridyl) benzimidazoles," Indian Journal of Chemistry, 2003, vol. 42B, pp. 2115-2118.
Ito et al., Pharmacological Studies of a New Non-steroidal Antiinflammatory Drug: 2-(5-Ethylpyridin-2-yl)benzimidazole (KB-1043), Arzneim-Forsch/Drug Res., 1982, vol. 32, pp. 49-55.
Japanese Patent Office, Japanese Office Action issued in corresponding JP Application No. 2009-519377, dated Nov. 7, 2011.
Kauffman et al., "Synthesis of Photophysical Properties of Fluorescent 2-Aryl-1,3-dialkylbenzimidazolium Ions and a 1-Alkyl-2-arylbenzimidazole with Exicted State Intramolecular Proton-Transfer," J. Heterocyclic Chem., 1994, vol. 31, pp. 957-965.

(Continued)

*Primary Examiner* — Patricia L Morris
(74) *Attorney, Agent, or Firm* — Sughrue Mion, PLLC

(57) ABSTRACT

Disclosed are biaryl benzoimidazo derivatives. They have an inhibitory effect on calcium influx in HEK cells, thereby showing a powerful antagonistic effect on a vanilloid receptor, and further have an analgesic effect, thereby being useful for preventing or treating pain, acute pain, chronic pain, neuropathic pain, postoperative pain, migraine, arthralgia, neuropathies, nerve injury, diabetic neuropathy, neurological illness, neurodermatitis, stroke, bladder hypersensitivity, irritable bowel syndrome, a respiratory disorder such as cough, asthma, and chronic obstructive pulmonary disease, burning, psoriasis, itching, vomiting, irritation of the skin, eyes, and mucous membranes, gastric-duodenal ulcers, inflammatory intestinal diseases, and inflammatory diseases.

6 Claims, No Drawings

OTHER PUBLICATIONS

Malamas et al., "Novel Benzofuran and Benzothiophene Biphenyls as Inhibitors of Protein Tyrosine Phosphatase 1B with Antihyperglycemic Properties," American Chemical Society, 2000, pp. 1293-1310.

Miskelly et al., "Using Spectral Information in Forensic Imaging," Forensic Science International, 2005, vol. 155, pp. 112-118.

Zied et al., "Synthesis of Some New Pyridines, Thienopyridines and Pyrido [2,3;4',5']thieno[3', 2'-d ]pyrimidin-8-ones From 2-acetylbenzoimidazole," Croatica Chemica Acta, 2005, vol. 78, No. 1, pp. 63-70.

Zoorob et al., "Synthesis of Pyridone Derivatives Michael Condensation with Ethyl Cyanoacetate, Cyanoacetamide and Acetoacetamide," Z. Naturforsch, 1976, pp. 1680-1684.

* cited by examiner

BIARYL BENZOLMIDAZOLE DERIVATIVES AND PHARMACEUTICAL COMPOSITION COMPRISING THE SAME

This is a National Stage application under 35 USC §371 of PCT/KR2007/003362 filed on Jul. 11, 2007, which claims priority from Korean patent application 10-2006-0065115, all of which are incorporated by reference.

TECHNICAL FIELD

The present invention relates to a novel biaryl benzoimidazole derivative, a method for preparing the same, and a pharmaceutical composition comprising the same, in which the biaryl benzoimidazole derivative functions as an antagonist of the vanilloid receptor (Capsaicin receptor; Transient Receptor Potential Channel, Vanilloid subfamily member 1; TRPV-1; Vanilloid receptor-1; VR-1).

BACKGROUND ART

The vanilloid receptor, the receptor for capsaicin (trans-8-methyl-N-vanillyl-6-nonenamide), has long been assumed to exist. Finally, it was cloned in 1997 and called vanilloid receptor subtype 1 (hereinafter referred to as "VR-1") by Caterina et al. (Caterina et al., Nature, 1997, 389, 816). Located on small unmyelinated nerve fibers (C-fibers) and myelinated nerve fibers (A-fibers), VR-1 is known as an ion channel which plays an important role in sensitizing pain stimuli by introducing the strong influx of cations such as calcium and sodium ions into the nerve endings upon activation in response to external or internal stimuli. External stimuli capable of activating VR-1 are reported to include heat and acids as well as vanilloid compounds (Tominaga et al., Neuron, 1998, 21, 531). As internal stimuli to VR-1, there are leukotriene metabolites such as 12-hydroperoxyeicosa tetraenoic acid (12-HPETE) (Hwang at al., PNAS, 2000, 97, 3655), and arachidonic acid derivatives such as anandamide (Premkumar et al., Nature, 2000, 408, 985).

On the basis of these physiological activities, VR-1 has attracted intensive attention as an integral controller playing a pivotal role in transferring various external injurable stimuli into nerve cells. According to a report, VR-1 knock-out mice responded like normal mice to general stimuli, but showed greatly reduced pain response to heat or thermal hyperalgesia, which reflects the importance of VR-1 against noxious stimuli (Caterina et al., Science, 2000, 288, 306).

VR-1 is concentratively expressed in primary sensory neurons (Caterina et al., Nature, 1997, 389, 816), which are responsible for controlling functions of internal organs such as the skin, the bones, the bladder, the gastrointestinal tract, the lungs, and so on. In addition, being distributed in other neurons on the central nervous system, the kidneys, the stomach, and T-cells (Nozawa et al., Neuroscience Letter, 2001, 309, 33; Yiangou et al., Lancet (North America Edition), 2001, 357, 1338; Birder et al., PNAS, 2001, 98, 13396) and throughout the entire body, VR-1 is inferred to play an important role in cell division and cellular signal control.

Indications found, thus far, to be associated with the control mechanism of the activity of VR-1 include pain, acute pain, chronic pain, neuropathic pain, postoperative pain, migraines, arthralgia, neuropathy, nerve injury, diabetic neuropathy, neurological illness, neurodermatitis, strokes, bladder hypersensitivity, irritable bowel syndrome, respiratory disorders such as asthma, chronic obstructive pulmonary disease, etc., irritation to the skin, eyes, and mucous membranes, itching, fever, gastric-duodenal ulcer, inflammatory intestinal diseases, and urge incontinence (Korean Pat. Laid-Open Publication No. 10-2004-0034804), and an anti-obestic effect (Pharmacol. Rev., 1986, 38, 179).

Based on pharmaceutical mechanisms, both agonists and antagonists of VR-1 may be used for the treatment of the above-mentioned diseases. Pain alleviating effects of VR-1 agonists show the pharmaceutical mechanism based on the desensitization of capsaicin-sensitive sensory nerves. That is, VR-1 agonists cause pain and irritation of sensory nerves so as to desensitize them to other noxious stimuli. Due to the induction of pain in the early stage, VR-1 agonists are developed only as local analgesics. In contrast, acting through the mechanism of blocking sensory nerves from recognizing pain signals, VR-1 antagonists do not cause early pain or irritation, and have been studied for use in the treatment of systemic diseases.

As compounds capable of modulating VR-1 activity, agonists such as capsaicin, DA-5018, resiniferatoxin, etc. are used as pain drugs or are under clinical study (Szallasi, J. Med chem., 2004, 47, 2717), while various agonists including amine compounds such as heterocycloalkylbenzoimidazole (WO2004095549), amide (WO03068749, WO2004069792, WO2006006740, WO2006006741, WO2004108133, US20060122231, US20050288281, GB200319150, SE200301246), (thio)urea (WO03080578, WO02072536, WO03022809, WO03055484, WO03029199, WO03053945, WO2004052845, WO2004007459, WO2005014580, U.S. Pat. Nos. 6,984,647, 7,015,233, GB200110901, GB200305426, CA2417507, JP2003-055209, KR0556158), quinazoline, heteroaryl etc. (WO03062209, WO2004055003, WO2004055004, WO2004033435, WO05003084, WO2004072068, WO2004002983, WO0208221, WO05009977, WO0216317, US20040157845, US20050113576, U.S. Pat. No. 6,933,311, U.S. Pat. No. 7,053,088, US20060084640, US20060089360, US20060058308, U.S. Pat. No. 6,974,818, GB200107505, GB200326217, GB200407748) as well as capsazepine and iodoresiniferatoxin are under study.

Recently, the present inventors have reported an antagonist having a structure of benzoimidazole as disclosed in WO2006/080821A1, in which the antagonist shows a powerful antagonistic effect on a vanilloid receptor in HEK cells, and a powerful analgesic effect in a writhing test using an animal model.

DISCLOSURE OF INVENTION

Technical Problem

The present inventors have conducted extensive studies on a compound regulating a VR-1 activity. As a result, they found that a novel biaryl benzoimidazole derivative is an excellent VR-1 antagonist, and confirmed that the derivative shows a powerful pharmacological effect (for example, effects on pain, inflammation, and ulcer) and excellent safety in an animal model, thereby completing the present invention.

Technical Solution

The present invention provides a novel biaryl benzoimidazole derivative having an excellent inhibitory effect on VR-1, or a pharmaceutically acceptable salt, solvate, or isomer thereof.

Further, the present invention provides a method for preparing the biaryl benzoimidazole derivative, or the pharmaceutically acceptable salt, solvate, or isomer thereof.

Further, the present invention provides a pharmaceutical composition comprising the biaryl benzoimidazole derivative, or the pharmaceutically acceptable salt, solvate, or isomer thereof.

BEST MODE FOR CARRYING OUT THE INVENTION

In one embodiment, the present invention provides a novel biaryl benzoimidazole derivative represented by the following Formula 1.

[Formula 1]

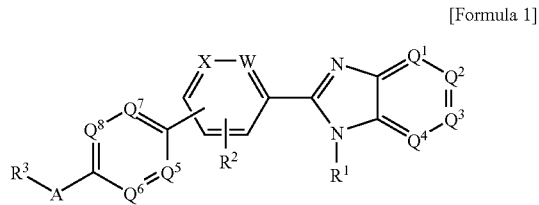

wherein, $R^1$ is hydrogen or $(CR^aR^{a'})_m R^b$;

m is an integer of 0, 1 or 2;

$R^a$ and $R^{a'}$ are each independently hydrogen; halogen; nitro; hydroxy; cyano; azide; amine; $NH(C_{1\sim6}$ alkyl); $N(C_{1\sim6}$ alkyl)$_2$; alkoxy having 1 to 8 carbon atoms; alkyl having 1 to 8 carbon atoms substituted or unsubstituted with one or more $R^c$; alkenyl having 2 to 8 carbon atoms substituted or unsubstituted with one or more $R^c$; phenyl substituted or unsubstituted with one or more $R^c$; or benzyl substituted or unsubstituted with one or more $R^c$;

$R^b$ is hydrogen; hydroxy; alkyl having 1 to 6 carbon atoms substituted or unsubstituted with one or more $R^c$; phenyl substituted or unsubstituted with one or more $R^c$; or benzyl substituted or unsubstituted with one or more $R^c$;

$R^c$ is halogen; cyano; nitro; azide; phenyl; benzyl; $C(=O)R^d$; $C(=O)OR^d$; $C(=O)NR^dR^{d'}$; $OR^d$; $OC(=O)R^e$; $OC(=O)OR^e$; $OC(=O)NR^dR^{d'}$; $OC_{1\sim6}$alkyl$OR^d$; $OC_{1\sim6}$alkylNR^dR^{d'}$; $SR^d$; $S(=O)R^e$; $S(=O)_2R^e$; $S(=O)_2NR^dR^{d'}$; $CR^d=NR^{d'}$; $NR^dR^{d'}$; $NR^dC(=O)R^e$; $NR^dC(=O)OR^e$; $NR^dC(=O)NR^{d'}R^{d''}$; $NR^d C(=NR^{d'})NR^{d''}R^{d'''}$; $NR^dS(=O)_2R^e$; $NR^dOR^{d'}$; $NR^dC_{1\sim6}$alkylNR$^{d'}R^{d''}$; or $NR^dC_{1\sim6}$alkyl$OR^{d'}$;

$R^d$, $R^{d'}$, $R^{d''}$ and $R^{d'''}$ are each independently hydrogen or $R^e$;

$R^e$ is phenyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl), and $N(C_{1\sim4}$ alkyl)$_2$;

benzyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl), and $N(C_{1\sim4}$ alkyl)$_2$;

alkyl having 1 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl), and $N(C_{1\sim4}$ alkyl)$_2$; or phosphoric acid;

$R^2$ is hydrogen; halogen; nitro; hydroxy; cyano; azide; amine; alkoxy having 1 to 8 carbon atoms; haloalkyl having 1 to 6 carbon atoms; haloalkoxy having 1 to 6 carbon atoms; alkyl having 1 to 10 carbon atoms substituted or unsubstituted with one or more $R^f$; alkenyl having 2 to 10 carbon atoms substituted or unsubstituted with one or more $R^f$; alkynyl having 2 to 10 carbon atoms substituted or unsubstituted with one or more $R^f$; cycloalkyl having 3 to 10 carbon atoms substituted or unsubstituted with one or more $R^f$; bicycloalkyl having 8 to 14 carbon atoms substituted or unsubstituted with one or more $R^f$; cycloalkenyl having 3 to 10 carbon atoms substituted or unsubstituted with one or more $R^f$; bicycloalkenyl having 8 to 14 carbon atoms substituted or unsubstituted with one or more $R^f$; heterocycloalkyl having 3 to 7 carbon atoms substituted or unsubstituted with one or more $R^f$; heterobicycloalkyl having 7 to 10 carbon atoms substituted or unsubstituted with one or more $R^f$; phenyl substituted or unsubstituted with one or more $R^f$; naphthyl substituted or unsubstituted with one or more $R^f$; benzyl substituted or unsubstituted with one or more $R^f$; heteroaryl having 5 to 10 carbon atoms substituted or unsubstituted with one or more $R^f$; $C(=O)R^d$; $C(=O)OR^d$; $C(=O)NR^dR^{d'}$; $OR^d$; $OC(=O)R^e$; $OC(=O)OR^e$; $OC(=O)NR^dR^{d'}$; $OC_{1\sim6}$alkyl$OR^d$; $OC_{1\sim6}$alkylNR$^dR^{d'}$; $SR^d$; $S(=O)R^e$; $S(=O)_2R^e$; $S(=O)_2NR^dR^{d'}$; $CR^d=NR^{d'}$; $NR^dR^{d'}$; $NR^dC(=O)R^e$; $NR^dC(=O)OR^e$; $NR^dC(=O)NR^{d'}R^{d''}$; $NR^dC(=NR^{d'})NR^{d''}R^{d'''}$; $NR^dS(=O)_2R^e$; $NR^dOR^{d'}$; $NR^dC_{1\sim6}$alkylNR$^{d'}R^{d''}$; or $NR^dC_{1\sim6}$alkyl$OR^{d'}$;

$R^f$ is alkyl having 1 to 6 carbon atoms; alkenyl having 2 to 6 carbon atoms; alkynyl having 2 to 6 carbon atoms; haloalkyl having 1 to 6 carbon atoms; haloalkoxy having 1 to 6 carbon atoms; halogen; azide; nitro; cyano; phenyl; benzyl; $C(=O)R^d$; $C(=O)OR^d$; $C(=O)NR^dR^{d'}$; $OR^d$; $OC(=O)R^e$; $OC(=O)OR^e$; $OC(=O)NR^dR^{d'}$; $OC_{1\sim6}$alkyl$OR^d$; $OC_{1\sim6}$alkylNR$^dR^{d'}$; $SR^d$; $S(=O)R^e$; $S(=O)_2R^e$; $S(=O)_2NR^dR^{d'}$; $CR^d=NR^{d'}$; $NR^dR^{d'}$; $NR^dC(=O)R^e$; $NR^dC(=O)OR^e$; $NR^dC(=O)NR^{d'}R^{d''}$; $NR^dC(=NR^{d'})NR^{d''}R^{d'''}$; $NR^dS(=O)_2R^e$; $NR^dOR^{d'}$; $NR^dC_{1\sim6}$alkylNR$^{d'}R^{d''}$; or $NR^dC_{1\sim6}$alkyl$OR^{d'}$;

A is $(CR^gR^{g'})_pZ$ or $Z(CR^gR^{g'})_p$;

p is an integer of 0, 1 or 2;

Z is $C(=O)$; $C(=O)O$; $C(=O)NR^d$; $C(=NR^d)$; $C(=NR^d)NR^{d'}$; $C(=O)C_{1\sim6}$alkyl$C(=O)$; $C(=O)C_{1\sim6}$alkylO; $C(=O)C_{1\sim6}$alkylS; $C(=O)C_{1\sim6}$alkylS$(=O)$; $C(=O)C_{1\sim6}$alkylNR$^d$; O; $OC(=O)$; $OC(=O)NR^d$; $OC(=O)NR^dS(=O)_2$; $OC_{1\sim6}$alkyl$C(=O)$; $OC_{1\sim6}$alkylO; $OC_{1\sim6}$alkylS; $OC_{1\sim6}$alkylS$(=O)$; $OC_{1\sim6}$alkylNR$^d$; S; $SC_{1\sim6}$alkyl$C(=O)$; $SC_{1\sim6}$alkylO; $SC_{1\sim6}$alkylS; $SC_{1\sim6}$alkylS$(=O)$; $SC_{1\sim6}$alkylNR$^d$; $S(=O)$; $S(=O)$; $S(=O)NR^d$; $S(=O)NR^d C(=O)$; $S(=O)_2NR^dC(=O)O$; $S(=O)_2NR^dC(=O)NR^d$; $S(=O)_2C_{1\sim6}$alkyl$C(=O)$; $S(=O)_2C_{1\sim6}$alkylO; $S(=O)_2C_{1\sim6}$alkylS$; $S(=O)_2C_{1\sim6}$alkylS$(=O)_2$; $S(=O)_2C_{1\sim6}$alkylNR$^d$; $NR^d$; $NR^d$; $C(=O)$; $NR^dC(=O)O$; $NR^dC(=O)NR^{d'}$; $NR^dC(=NR^{d'})NR^{d''}$; $NR^dS(=O)_2$; $NR^dS(=O)NR^{d'}$; $NR^dC_{1\sim6}$alkyl$C(=O)$; $NR^dC_{1\sim6}$alkylO; $NR^dC_{1\sim6}$alkylS; $NR^dC_{1\sim6}$alkylS$(=O)$; or $NR^dC_{1\sim6}$alkylNR$^{d'}$;

$R^g$ and $R^{g'}$ are each independently hydrogen; halogen; nitro; hydroxy; cyano; azide; amine; $NH(C_{1\sim6}$ alkyl); $N(C_{1\sim6}$ alkyl)$_2$; alkoxy having 1 to 8 carbon atoms; alkyl having 1 to 8 carbon atoms substituted or unsubstituted with one or more $R^c$; alkenyl having 2 to 8 carbon atoms substituted or unsubstituted with one or more $R^c$; phenyl substituted or unsubstituted with one or more $R^c$; or benzyl substituted or unsubstituted with one or more $R^c$;

$R^3$ is hydrogen; halogen; nitro; hydroxy; cyano; azide; amine; alkoxy having 1 to 8 carbon atoms; haloalkyl having 1 to 6 carbon atoms; haloalkoxy having 1 to 6 carbon atom; alkyl having 1 to 10 carbon atoms substituted or unsubstituted with one or more $R^f$; alkenyl having 2 to 10 carbon atoms substituted or unsubstituted with one or more $R^f$; alkynyl having 2 to 10 carbon atoms substituted or unsubstituted with one or more $R^f$; cycloalkyl having 3 to 10 carbon atoms substituted or unsubstituted with one or more $R^f$; bicycloalkyl having 8 to 14 carbon atoms substituted or unsubstituted with one or more $R^f$; cycloalkenyl having 3 to 10 carbon atoms substituted or unsubstituted with one or more $R^f$; bicycloalkenyl having 8 to 14 carbon atoms substituted or unsubstituted with one or more $R^f$; heterocycloalkyl having 3 to 7 carbon atoms substituted or unsubstituted with one or more $R^f$; heterobicycloalkyl having 7 to 10 carbon atoms substituted or unsubstituted with one or more $R^f$; phenyl substituted or unsubstituted with one or more $R^f$; naphthyl substituted or unsubstituted with one or more $R^f$; benzyl substituted or unsubstituted with one or more $R^f$; or heteroaryl having 5 to 10 carbon atoms substituted or unsubstituted with one or more $R^f$;

$Q^1$ is N or $CR^4$;
$Q^2$ is N or $CR^5$;
$Q^3$ is N or $CR^{5'}$;
$Q^4$ is N or $CR^{4'}$;
$Q^5$ is N or $CR^6$;
$Q^6$ is N or $CR^7$;
$Q^7$ is N or $CR^{6'}$;
$Q^8$ is N or $CR^{7'}$;
W is N or $CR^8$;
X is N or $CR^{8'}$;

$R^4$, $R^{4'}$, $R^5$, $R^{5'}$, $R^6$, $R^{6'}$, $R^7$ and $R^{7'}$ are the same or different from each other, and each independently hydrogen; halogen; nitro; hydroxy; cyano; azide; amine; alkoxy having 1 to 8 carbon atoms; haloalkyl having 1 to 6 carbon atoms; haloalkoxy having 1 to 6 carbon atoms; alkyl having 1 to 10 carbon atoms substituted or unsubstituted with one or more $R^h$; alkenyl having 2 to 10 carbon atoms substituted or unsubstituted with one or more $R^h$; alkynyl having 2 to 10 carbon atoms substituted or unsubstituted with one or more $R^h$; cycloalkyl having 3 to 10 carbon atoms substituted or unsubstituted with one or more $R^h$; bicycloalkyl having 8 to 14 carbon atoms substituted or unsubstituted with one or more $R^h$; cycloalkenyl having 3 to 10 carbon atoms substituted or unsubstituted with one or more $R^h$; bicycloalkenyl having 8 to 14 carbon atoms substituted or unsubstituted with one or more $R^h$; heterocycloalkyl having 3 to 7 carbon atoms substituted or unsubstituted with one or more $R^h$; heterobicycloalkyl having 7 to 10 carbon atoms substituted or unsubstituted with one or more $R^h$; phenyl substituted or unsubstituted with one or more $R^h$; naphthyl substituted or unsubstituted with one or more $R^h$; benzyl substituted or unsubstituted with one or more $R^h$; heteroaryl having 5 to 10 carbon atoms substituted or unsubstituted with one or more $R^h$; $C(=O)R^i$; $C(=O)OR^i$; $C(=O)NR^iR^{i'}$; $OR^i$; $OC(=O)R^j$; $OC(=O)OR^j$; $OC(=O)NR^iR^{i'}$; $OC_{1\sim6}$alkyl$OR^i$; $OC_{1\sim6}$alkyl$NR^iR^{i'}$; $SR^i$; $S(=O)R^j$; $S(=O)_2R^j$; $S(=O)_2NR^iR^{i'}$; $CR^i=NR^{i'}$; $NR^iR^{i'}$; $NR^iC(=O)R^j$; $NR^iC(=O)OR^j$; $NR^iC(=O)NR^{i'}R^{i''}$; $NR^iC(=NR^{i'})NR^{i''}R^{i'''}$; $NR^iS(=O)_2R^j$; $NR^iOR^{i'}$; $NR^iC_{1\sim6}$alkyl$NR^{i'}R^{i''}$; $NR^iC_{1\sim6}$alkyl$OR^{i'}$; the two groups of $R^4$ and $R^5$, or $R^{4'}$ and $R^{5'}$ may form a 5-, 6-, or 7-membered, saturated, partially saturated, or unsaturated monocyclic compound which is mono, di, tri, or tetra substituted or unsubstituted with an atom selected from nitrogen, oxygen, and sulfur; the two groups of $R^4$ and $R^5$, or $R^{4'}$ and $R^{5'}$ may form a 6-, 7-, 8-, 9-, 10-, or 11-membered, saturated, partially saturated, or unsaturated bicyclic compound which is mono, di, tri, or tetra substituted or unsubstituted with an atom selected from nitrogen, oxygen, and sulfur; the two groups of $R^6$ and $R^7$, or $R^{6'}$ and $R^{7'}$ may form a 5-, 6- or 7-membered, saturated, partially saturated, or unsaturated monocyclic compound which is mono, di, tri, or tetra substituted or unsubstituted with an atom selected from nitrogen, oxygen, and sulfur; or the two groups of $R^6$ and $R^7$, or $R^{6'}$ and $R^{7'}$ may form a 6-, 7-, 8-, 9-, 10-, or 11-membered, saturated, partially saturated, or unsaturated bicyclic compound which is mono, di, tri, or tetra substituted or unsubstituted with an atom selected from nitrogen, oxygen, and sulfur;

$R^h$ is alkyl having 1 to 6 carbon atoms; alkenyl having 2 to 6 carbon atoms; alkynyl having 2 to 6 carbon atoms; cycloalkyl having 3 to 8 carbon atoms; cycloalkenyl having 5 to 8 carbon atoms; heterocycloalkyl having 3 to 5 carbon atoms; haloalkyl having 1 to 6 carbon atoms; haloalkoxy having 1 to 6 carbon atoms; halogen; azide; nitro; cyano; phenyl; benzyl; $C(=O)R^i$; $C(=O)OR^i$; $C(=O)NR^iR^{i'}$; $OR^i$; $OC(=O)R^j$; $OC(=O)OR^j$; $OC(=O)NR^iR^{i'}$; $OC_{1\sim6}$alkyl$OR^i$; $OC_{1\sim6}$alkyl$NR^iR^{i'}$; $SR^i$; $S(=O)R^j$; $S(=O)_2R^j$; $S(=O)_2NR^iR^{i'}$; $CR^i=NR^{i'}$; $NR^iR^{i'}$; $NR^iC(=O)R^j$; $NR^iC(=O)OR^j$; $NR^dC(=O)NR^iR^{i'}$; $NR^iC(=NR^i)NR^{i''}R^{i'''}$; $NR^iS(=O)_2R^j$; $NR^iOR^{i'}$; $NR^iC_{1\sim6}$alkyl$NR^iR^{i''}$; $NR^iC_{1\sim6}$alkyl$OR^{i'}$ $R^i$, $R^{i'}$, $R^{i''}$ and $R^{i'''}$ are each independently hydrogen or $R^j$;

$R^j$ is phenyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$;

benzyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$;

alkyl having 1 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$;

alkenyl having 2 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$;

alkynyl having 2 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$;

cycloalkyl having 3 to 8 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$;

cycloalkenyl having 5 to 8 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$;

heterocycloalkyl having 3 to 5 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl$)$ and $N(C_{1\sim4}$ alkyl$)_2$; or phosphoric acid;

$R^8$ and $R^{8'}$ are the same or different from each other, and each independently hydrogen; halogen; hydroxy; cyano; azide; amine; alkoxy having 1 to 8 carbon atoms; haloalkyl having 1 to 6 carbon atoms; haloalkoxy having 1 to 6 carbon atoms; alkyl having 1 to 10 carbon atoms substituted or unsubstituted with one or more $R^h$; alkenyl having 2 to 10 carbon atoms substituted or unsubstituted with one or more $R^h$; alkynyl having 2 to 10 carbon atoms substituted or unsubstituted with one or more $R^h$; cycloalkyl having 3 to 10 carbon atoms substituted or unsubstituted with one or more $R^h$; bicycloalkyl having 8 to 14 carbon atoms substituted or unsubstituted with one or more $R^h$; cycloalkenyl having 3 to 10 carbon atoms substituted or unsubstituted with one or more $R^h$; bicycloalkenyl having 8 to 14 carbon atoms substituted or unsubstituted with one or more $R^h$; heterocycloalkyl having 3 to 7 carbon atoms substituted or unsubstituted with one or more $R^h$; heterobicycloalkyl having 7 to 10 carbon atoms substituted or unsubstituted with one or more $R^h$; phenyl substituted or unsubstituted with one or more $R^h$; naphthyl substituted or unsubstituted with one or more $R^h$; benzyl substituted or unsubstituted with one or more $R^h$; heteroaryl having 5 to 10 carbon atoms substituted or unsubstituted with one or more $R^h$; $C(=O)R^i$; $C(=O)OR^i$; $C(=O)NR^iR^{i'}$; $OR^i$; $OC(=O)R^i$; $OC(=O)OR^i$; $OC(=O)NR^iR^{i'}$; $OC_{1\sim6}alkylOR^i$; $OC_{1\sim6}alkylNR^iR^{i'}$; $SR^i$; $S(=O)R^i$; $S(=O)_2R^i$; $S(=O)NR^iR^{i'}$; $CR^i=NR^iR^{i'}$; $NR^iR^{i'}$; $NR^iC(=O)R^i$; $NR^iC(=O)OR^i$; $NR^iC(=O)NR^{i'}R^{i''}$; $NR^iC(=NR^{i'})NR^{i''}R^{i'''}$; $NR^iS(=O)_2R^i$; $NR^iOR^{i'}$; $NR^iC_{1\sim6}alkylNR^{i'}R^{i''}$; $NR^iC_{1\sim6}alkylOR^i$; the two groups of $R^8$ and $R^{8'}$ may form a 5-, 6- or 7-membered, saturated, partially saturated, or unsaturated monocyclic compound which is mono, di, tri, or tetra substituted or unsubstituted with an atom selected from nitrogen, oxygen, and sulfur; or the two groups of $R^8$ and $R^{8'}$ may form a 6-, 7-, 8-, 9-, 10-, or 11-membered, saturated, partially saturated, or unsaturated dicyclic compound which is mono, di, tri, or tetra substituted or unsubstituted with an atom selected from nitrogen, oxygen, and sulfur.

In a preferred embodiment, a preferred compound among biaryl benzoimidazole derivatives of Formula 1 of the present invention is specifically as follows:

1) {5-chloro-6-[4-(6-morpholin-4-yl-1H-benzoimidazol-2-yl)-phenyl]-pyridin-3-yl}-methanol,
2) (5-chloro-6-{4-[6-(4-methyl-piperazin-1-yl)-1H-benzoimidazol-2-yl]-phenyl}-pyridin-3-yl)-methanol,
3) {5-chloro-6-[4-(6-trifluoromethyl-1H-benzoimidazol-2-yl)-phenyl]-pyridin-3-yl}-methanol,
4) {6-[4-(6-tert-butyl-1H-benzoimidazol-2-yl)-phenyl]-5-chloro-pyridin-3-yl}-methanol,
5) {6-[4-(6-bromo-1H-benzoimidazol-2-yl)-phenyl]-5-chloro-pyridin-3-yl}-methanol,
6) {6-[4-(6-bromo-1H-imidazo[4,5-b]pyridin-2-yl)-phenyl]-5-chloro-pyridin-3-yl}-methanol,
7) {6-[4-(4-bromo-6-trifluoromethyl-1H-benzoimidazol-2-yl)-phenyl]-5-chloro-pyridin-3-yl}-methanol,
8) {5-chloro-6-[4-(4,6-dibromo-1H-benzoimidazol-2-yl)-phenyl]-pyridin-3-yl}-methanol,
9) 5-chloro-6-[4-(6-trifluoromethyl-1H-benzoimidazol-2-yl)-phenyl]-nicotinic acid,
10) 6-[4-(6-tert-butyl-1H-benzoimidazol-2-yl)-phenyl]-5-chloro-nicotinic acid,
11) 6-[4-(6-bromo-1H-benzoimidazol-2-yl)-phenyl]-5-chloro-nicotinic acid,
12) 6-[4-(6-bromo-1H-imidazo[4,5-b]pyridin-2-yl)-phenyl]-5-chloro-nicotinic acid,
13) 6-[4-(4-bromo-6-trifluoromethyl-1H-benzoimidazol-2-yl)-phenyl]-5-chloro-nicotinic acid,
14) 5-chloro-6-[4-(6-trifluoromethyl-1H-benzoimidazol-2-yl)-phenyl]-nicotinic acid methyl ester,
15) 6-[4-(6-tert-butyl-1H-benzoimidazol-2-yl)-phenyl]-5-chloro-nicotinic acid methyl ester,
16) 6-[4-(6-bromo-1H-benzoimidazol-2-yl)-phenyl]-5-chloro-nicotinic acid methyl ester,
17) 6-[4-(6-bromo-1H-imidazo[4,5-b]pyridin-2-yl)-phenyl]-5-chloro-nicotinic acid methyl ester,
18) 6-[4-(4-bromo-6-trifluoromethyl-1H-benzoimidazol-2-yl)-phenyl]-5-chloro-nicotinic acid methyl ester,
19) acetic acid 5-chloro-6-[4-(6-trifluoromethyl-1H-benzoimidazol-2-yl)-phenyl]-pyridin-3-yl methyl ester,
20) acetic acid 6-[4-(6-tert-butyl-1H-benzoimidazol-2-yl)-phenyl]-5-chloro-pyridin-3-yl methyl ester,
21) acetic acid 6-[4-(6-bromo-1H-benzoimidazol-2-yl)-phenyl]5-chloro-pyridin-3-yl methyl ester,
22) acetic acid 6-[4-(6-bromo-1H-imidazo[4,5-b]pyridin-2-yl)-phenyl]-5-chloro-pyridin-3-yl methyl ester,
23) acetic acid 6-[4-(4-bromo-6-trifluoromethyl-1H-benzoimidazol-2-yl)-phenyl]-5-chloro-pyridin-3-yl methyl ester,
24) 5-chloro-N-ethyl-6-[4-(6-trifluoromethyl-1H-benzoimidazol-2-yl)-phenyl]-nicotinamide,
25) 6-[4-(6-tert-butyl-1H-benzoimidazol-2-yl)-phenyl]-5-chloro-N-ethyl-nicotinamide,
26) 6-[4-(6-bromo-1H-benzoimidazol-2-yl)-phenyl]-5-chloro-N-ethyl-nicotinamide,
27) 6-[4-(6-bromo-1H-imidazo[4,5-b]pyridin-2-yl)-phenyl]-5-chloro-N-ethyl-nicotinamide,
28) 6-[4-(4-bromo-6-trifluoromethyl-1H-benzoimidazol-2-yl)-phenyl]-5-chloro-N-ethyl-nicotinamide,
29) 3-chloro-6'-(6-morpholin-4-yl-1H-benzoimidazol-2-yl)-[2,3']bipyridinyl-5-carboxylic acid methyl ester,
30) 3-chloro-6'-[6-(4-methyl-piperazin-1-yl)-1H-benzoimidazol-2-yl]-[2,3']bipyridinyl-5-carboxylic acid methyl ester,
31) 3-chloro-6'-(6-trifluoromethyl-1H-benzoimidazol-2-yl)-[2,3']bipyridinyl-5-carboxylic acid methyl ester,
32) 6'-(6-tert-butyl-1H-benzoimidazol-2-yl)-3-chloro-[2,3']bipyridinyl-5-carboxylic acid methyl ester,
33) 6'-(6-bromo-1H-benzoimidazol-2-yl)-3-chloro-[2,3']bipyridinyl-5-carboxylic acid methyl ester,
34) 6'-(6-bromo-1H-imidazo[4,5-b]pyridin-2-yl)-3-chloro-[2,3']bipyridinyl-5-carboxylic acid methyl ester,
35) 6'-(4-bromo-6-trifluoromethyl-1H-benzoimidazol-2-yl)-3-chloro-[2,3']bipyridinyl-5-carboxylic acid methyl ester,
36) 3-chloro-6'-(4,6-dibromo-1H-benzoimidazol-2-yl)-[2,3']bipyridinyl-5-carboxylic acid methyl ester,
37) 3-chloro-6'-(6-morpholin-4-yl-1H-benzoimidazol-2-yl)-[2,3']bipyridinyl-5-carboxylic acid,
38) 3-chloro-6'-[6-(4-methyl-piperazin-1-yl)-1H-benzoimidazol-2-yl]-[2,3']bipyridinyl-5-carboxylic acid,
39) 3-chloro-6'-(6-trifluoromethyl-1H-benzoimidazol-2-yl)-[2,3']bipyridinyl-5-carboxylic acid,
40) 6'-(6-tert-butyl-1H-benzoimidazol-2-yl)-3-chloro-[2,3']bipyridinyl-5-carboxylic acid,
41) 6'-(6-bromo-1H-benzoimidazol-2-yl)-3-chloro-[2,3']bipyridinyl-5-carboxylic acid,
42) 6'-(6-bromo-1H-imidazo[4,5-b]pyridin-2-yl)-3-chloro-[2,3']bipyridinyl-5-carboxylic acid,
43) 6'-(4-bromo-6-trifluoromethyl-1H-benzoimidazol-2-yl)-3-chloro-[2,3']bipyridinyl-5-carboxylic acid,
44) 3-chloro-6'-(4,6-dibromo-1H-benzoimidazol-2-yl)-[2,3']bipyridinyl-5-carboxylic acid,
45) [3-chloro-6'-(6-morpholin-4-yl-1H-benzoimidazol-2-yl)-[2,3']bipyridinyl-5-yl]-methanol,
46) {3-chloro-6'-[6-(4-methyl-piperazin-1-yl)-1H-benzoimidazol-2-yl]-[2,3']bipyridinyl-5-yl}-methanol,
47) [3-chloro-6'-(6-trifluoromethyl-1H-benzoimidazol-2-yl)-[2,3']bipyridinyl-5-yl]-methanol,
48) [6'-(6-tert-butyl-1H-benzoimidazol-2-yl)-3-chloro-[2,3']bipyridinyl-5-yl]-methanol, 49) [6'-(6-bromo-1H-benzoimidazol-2-yl)-3-chloro-[2,3']bipyridinyl-5-yl]-methanol,
50) [6'-(6-bromo-1H-imidazo[4,5-b]pyridin-2-yl)-3-chloro-[2,3']bipyridinyl-5-yl]-methanol,
51) [6'-(4-bromo-6-trifluoromethyl-1H-benzoimidazol-2-yl)-3-chloro-[2,3']bipyridinyl-5-yl]-methanol,
52) [3-chloro-6'-(4,6-dibromo-1H-benzoimidazol-2-yl)-[2,3']bipyridinyl-5-yl]-methanol,
53) 3-chloro-6'-(6-morpholin-4-yl-1H-benzoimidazol-2-yl)-[2,3']bipyridinyl-5-carboxylic acid ethyl amide,
54) 3-chloro-6'-[6-(4-methyl-piperazin-1-yl)-1H-benzoimidazol-2-yl]-[2,3']bipyridinyl-5-carboxylic acid ethyl amide,
55) 3-chloro-6'-(6-trifluoromethyl-1H-benzoimidazol-2-yl)-[2,3']bipyridinyl-5-carboxylic acid ethyl amide,
56) 6'-(6-tert-butyl-1H-benzoimidazol-2-yl)-3-chloro-[2,3']bipyridinyl-5-carboxylic acid ethyl amide,
57) 6'-(6-bromo-1H-benzoimidazol-2-yl)-3-chloro-[2,3']bipyridinyl-5-carboxylic acid ethyl amide,
58) 6'-(6-bromo-1H-imidazo[4,5-b]pyridin-2-yl)-3-chloro-[2,3']bipyridinyl-5-carboxylic acid ethyl amide,
59) 6'-(4-bromo-6-trifluoromethyl-1H-benzoimidazol-2-yl)-3-chloro-[2,3']bipyridinyl-5-carboxylic acid ethyl amide,
60) 3-chloro-6'-(4,6-dibromo-1H-benzoimidazol-2-yl)-[2,3']bipyridinyl-5-carboxylic acid ethyl amide,
61) 5-chloro-6-[4-(6-trifluoromethyl-1H-benzoimidazol-2-yl)-phenyl]-pyridine-3-carbaldehyde,
62) 6-[4-(6-tert-butyl-1H-benzoimidazol-2-yl)-phenyl]-5-chloro-pyridine-3-carbaldehyde,
63) 6-[4-(6-bromo-1H-benzoimidazol-2-yl)-phenyl]-5-chloro-pyridine-3-carbaldehyde,
64) 2-[4-(5-bromomethyl-3-chloro-pyridin-2-yl)-phenyl]-6-trifluoromethyl-1H-benzoimidazole,
65) 2-[4-(5-bromomethyl-3-chloro-pyridin-2-yl)-phenyl]-6-tert-butyl-1H-benzoimidazole,
66) 6-bromo-2-[4-(5-bromomethyl-3-chloro-pyridin-2-yl)-phenyl]-1H-benzoimidazole,
67) 2-[4-(3-chloro-5-vinyl-pyridin-2-yl)-phenyl]-6-trifluoromethyl-1H-benzoimidazole,
68) 6-tert-butyl-2-[4-(3-chloro-5-vinyl-pyridin-2-yl)-phenyl]-1H-benzoimidazole,
69) 6-bromo-2-[4-(3-chloro-5-vinyl-pyridin-2-yl)-phenyl]-1H-benzoimidazole,
70) 6-chloro-2-[4-(3-chloro-5-vinyl-pyridin-2-yl)-phenyl]-1H-benzoimidazole,
71) 4-bromo-2-[4-(3-chloro-5-vinyl-pyridin-2-yl)-phenyl]-6-trifluoromethyl-1H-benzoimidazole,
72) 6'-(6-tert-butyl-1H-benzoimidazol-2-yl)-3-chloro-5-vinyl-[2,3']bipyridinyl,
73) 3-chloro-6'-(6-trifluoromethyl-1H-benzoimidazol-2-yl)-5-vinyl-[2,3']bipyridinyl,
74) 6'-(6-bromo-1H-benzoimidazol-2-yl)-3-chloro-5-vinyl-[2,3']bipyridinyl,
75) 3-chloro-6'-(6-chloro-1H-benzoimidazol-2-yl)-5-vinyl-[2,3']bipyridinyl, and
76) 6'-(4-bromo-6-trifluoromethyl-1H-benzoimidazol-2-yl)-3-chloro-5-vinyl-[2,3']bipyridinyl.

The biaryl benzoimidazole derivative of Formula 1 of the present invention can be prepared as a pharmaceutically acceptable salt according to a conventional method known in the art. The pharmaceutically acceptable salt is a conventional salt used in the related art such as acid addition salt, and comprises salts described in the article, J. Pharm. Sci., 1977, 66, 1. The pharmaceutically acceptable acid addition salt include an inorganic acid addition salt prepared with an inorganic acid such as hydrochloric acid, hydrobromic acid, phosphoric acid, ortho-phosphoric acid or sulfuric acid, or an organic acid addition salt prepared with an organic acid such as methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid, or acetylsalicylic acid.

Further, a pharmaceutically acceptable metal salt can be prepared using a base. An alkali metal salt and alkaline earth metal salt can be obtained by a method, in which a compound is dissolved in an excessive amount of alkali metal hydroxide or alkaline earth metal hydroxide solution, filtered the undissolved salt, and then the filtrate is evaporated and dried. In respects to metal salts, it is preferable that sodium, potassium, or calcium salt is pharmaceutically preferable, and the corresponding silver salt is obtained by reacting alkali metal salt or alkaline earth metal salt with a suitable silver salt (e.g. nitrate).

A salt and/or solvate of the compound of Formula 1 being not pharmaceutically acceptable can be used as an intermediate in the preparation of a salt and/or solvate of the compound of Formula 1 being pharmaceutically acceptable, or the compound of Formula 1 itself, which forms another aspect of the present invention.

The compound of Formula 1 of the invention can be prepared in a crystalline or noncrystalline form, and in the case of a crystalline form, the compound may be hydrated or solvated. In the scope of the invention, a stoichiometric hydrate as well as a compound containing various amount of water can be included.

The solvate includes a pharmaceutically acceptable solvate such as hydrate. The solvate includes a stoichiometric solvate and a nonstoichiometric solvate.

Further, the biaryl benzoimidazole derivative of Formula 1 of the invention has an asymmetric center, thereby existing in the form of a different enantiomer, and all of the optical isomers, R or S type stereoisomer, and a mixture thereof of the biaryl benzoimidazole derivative of Formula 1 are included in the scope of the invention.

In another embodiment, the present invention provides a method for preparing the biaryl benzoimidazole derivative of Formula 1. The method of the invention can be chemically prepared by the method illustrated in the following Reaction Schemes, but are not limited thereto. The following Reaction Schemes illustrates a method for preparing the representative compounds of the invention, and other compounds can be prepared by the modification of reagents and starting material known to those skilled in the art.

The method for preparing the compound of Formula 1 of the invention is illustrated as shown in the following Reaction Schemes 1 to 26.

[Reaction Scheme 1]

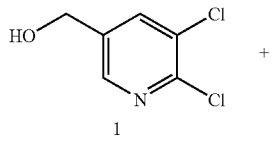

-continued

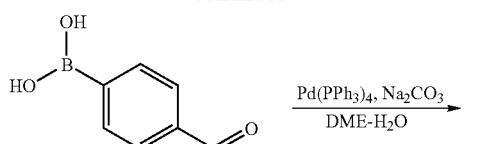

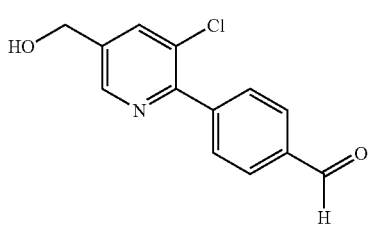

As shown in Reaction Scheme 1, (5,6-dichloro-3-yl) methanol is reacted with boronic acid in the presence of a palladium catalyst and a base to prepare a compound 3 (Tapolcsanyi et. al., Tetrahedron, 2002, 58, 10137).

[Reaction Scheme 2]

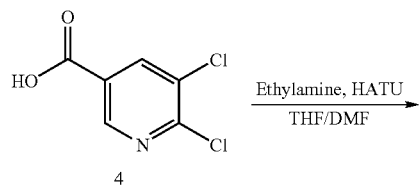

As shown in Reaction Scheme 2, a compound 4 is reacted with amine to prepare a compound 5.

[Reaction Scheme 3]

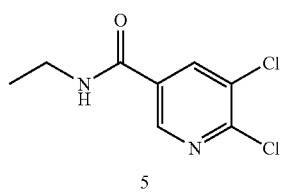

-continued

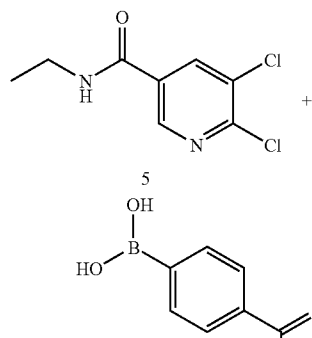

As shown in Reaction Scheme 3,5,6-dichloro-N-ethylnicotinamide is reacted with boronic acid in the presence of a palladium catalyst and a base to prepare a compound 6 (Tapolcsanyi et. al., Tetrahedron, 2002, 58, 10137).

[Reaction Scheme 4]

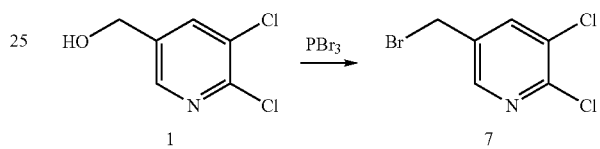

As shown in Reaction Scheme 4, the compound 1 is reacted with PBr₃ to prepare compound 7.

[Reaction Scheme 5]

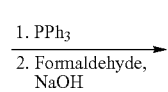

As shown in Reaction Scheme 5, the compound 7 is reacted with PPh₃ and formaldehyde in the presence of a base to prepare a compound 8.

[Reaction Scheme 6]

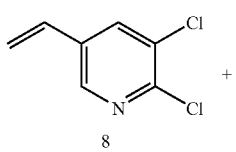

13

-continued

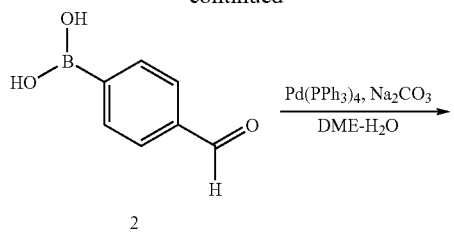

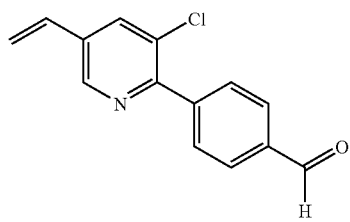

As shown in Reaction Scheme 6, a compound 8 is reacted with boronic acid in the presence of a palladium catalyst and a base to prepare a compound 9 (Tapolcsanyi et. al., Tetrahedron, 2002, 58, 10137).

[Reaction Scheme 7]

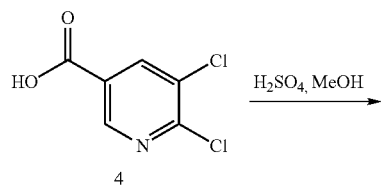

As shown in Reaction Scheme 7, 5,6-dichloronicotinic acid is reacted with methanol in the presence of an acid catalyst to prepare a compound 10 (C. K. Patel et. al., Bioorg. Med. Chem. Lett., 2004, 14, 605).

[Reaction Scheme 8]

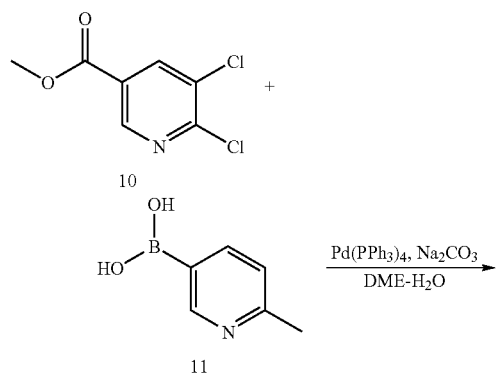

14

-continued

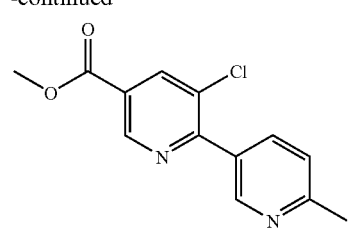

As shown in Reaction Scheme 8, the compound 10 is reacted with boronic acid in the presence of a palladium catalyst and a base to prepare a compound 12 (Tapolcsanyi et. al., Tetrahedron, 2002, 58, 10137).

[Reaction Scheme 9]

As shown in Reaction Scheme 9, the compound 12 is reacted with selenium dioxide to prepare a compound 13 (Glodberg et. al., Journal of Medicinal Chemistry, 2003, 46, 1337).

[Reaction Scheme 10]

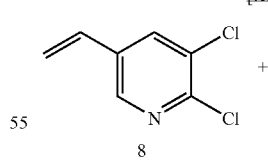

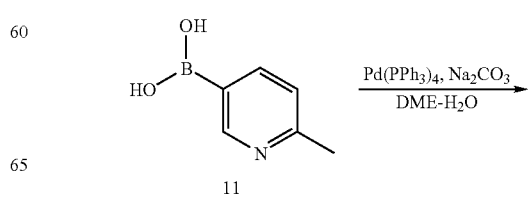

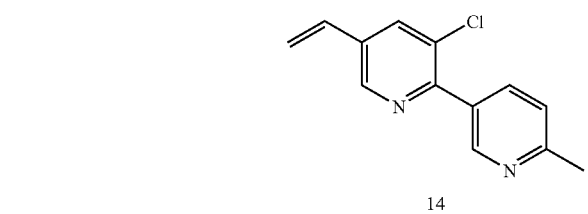

14

As shown in Reaction Scheme 10, the compound 8 is reacted with boronic acid in the presence of a palladium catalyst and a base to prepare a compound 14 (Tapolcsanyi et. al., Tetrahedron, 2002, 58, 10137).

[Reaction Scheme 11]

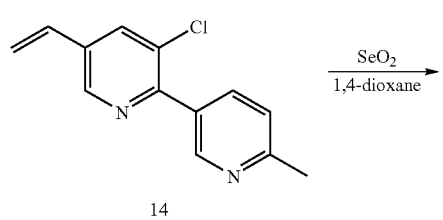

14

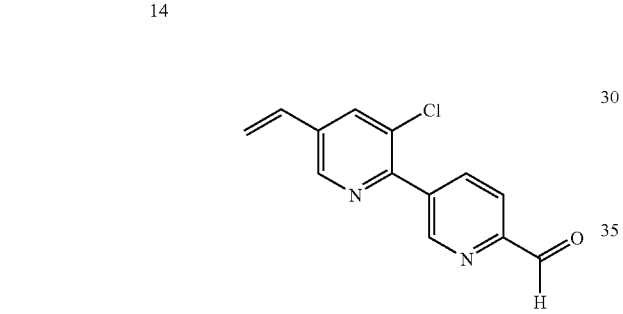

15

As shown in Reaction Scheme 11, the compound 14 is reacted with selenium dioxide to prepare a compound 15 (Glodberg et. al., Journal of Medicinal Chemistry, 2003, 46, 1337).

[Reaction Scheme 12]

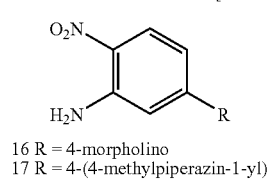

16 R = 4-morpholino
17 R = 4-(4-methylpiperazin-1-yl)

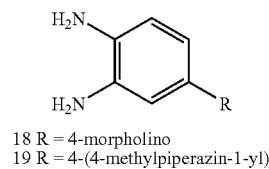

18 R = 4-morpholino
19 R = 4-(4-methylpiperazin-1-yl)

As shown in Reaction Scheme 12, the compound 16 or 17 is subjected to reduction reaction with hydrogen in the presence of a palladium/carbon catalyst to prepare a compound 18 or 19.

[Reaction Scheme 13]

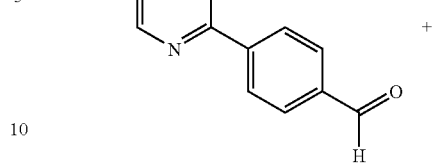

3

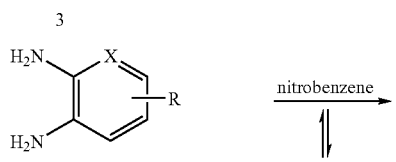

18 X = C, R = 4-morpholino
19 X = C, R = 4-(4-methylpiperazin-1-yl)
20 X = C, R = 4-(trifluoromethyl)
21 X = C, R = 4-tert-butyl
22 X = C, R = 4-bromo
23 X = N, R = 5-bromo
24 X = C, R = 3-bromo-5-trifluoromethyl
25 X = C, R = 3,5-dibromo 26 X = C, R = 6-morpholino
27 X = C, R = 6-(4-methylpiperazin-1-yl)
28 X = C, R = 6-(trifluoromethyl)
29 X = C, R = 6-tert-butyl
30 X = C, R = 6-bromo
31 X = N, R = 6-bromo
32 X = C, R = 4-bromo-6-trifluoromethyl
33 X = C, R = 4,6-dibromo As shown in Reaction Scheme 13, the compound 3 prepared in Reaction Scheme 1, the compounds 18 and 19 prepared in Reaction Scheme 12, and commercial compounds 20 to 25 are reacted in the presence of nitrobenzene to prepare compounds 26 to 33 (L. Garuti et. al., I L Farmaco, 2004, 59, 663).

[Reaction Scheme 14]

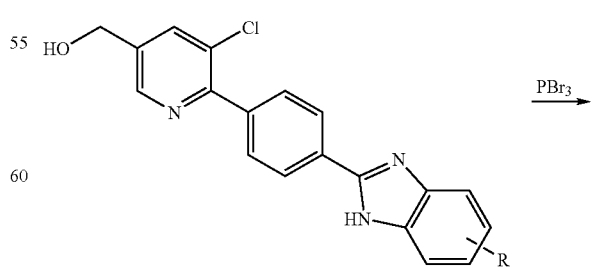

28 R = 6-(trifluoromethyl)
29 R = 6-tert-butyl
30 R = 6-bromo

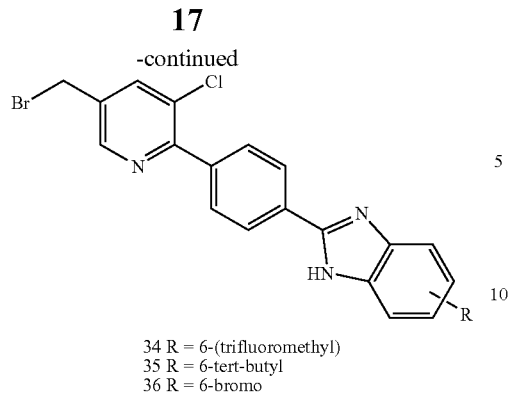

34 R = 6-(trifluoromethyl)
35 R = 6-tert-butyl
36 R = 6-bromo

As shown in Reaction Scheme 14, the compounds 28 to 30 prepared in Reaction Scheme 13 are reacted with PBr₃ to prepare compounds 34 to 36.

[Reaction Scheme 15]

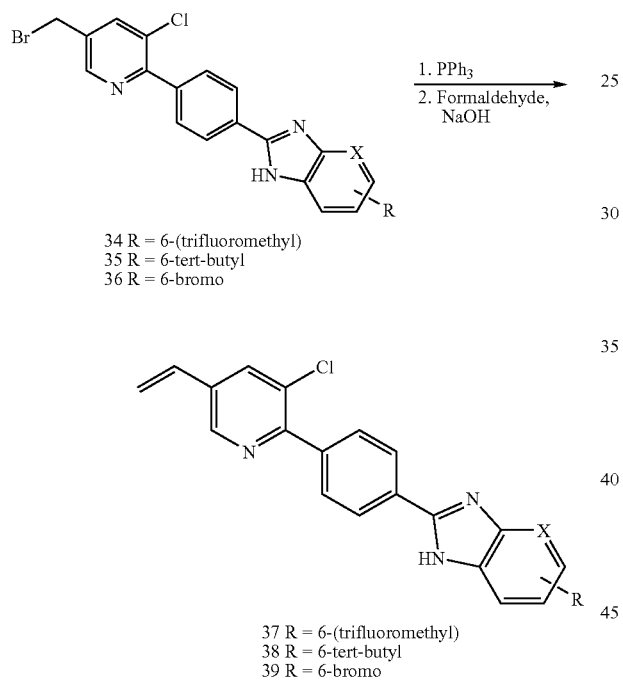

34 R = 6-(trifluoromethyl)
35 R = 6-tert-butyl
36 R = 6-bromo

37 R = 6-(trifluoromethyl)
38 R = 6-tert-butyl
39 R = 6-bromo

As shown in Reaction Scheme 15, the compounds 34 to 36 prepared in Reaction Scheme 14 are reacted with PPh₃ and formaldehyde in the presence of a base to prepare compounds 37 to 39.

[Reaction Scheme 16]

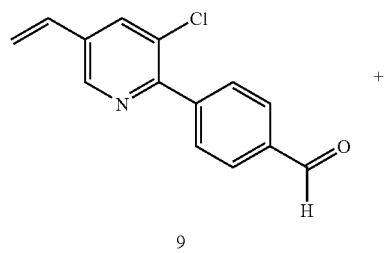

9

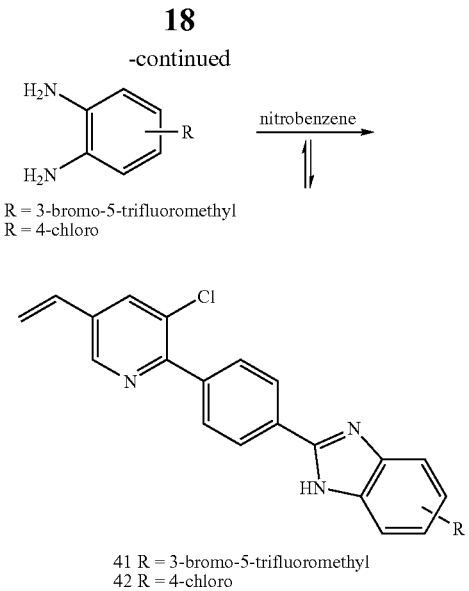

24 R = 3-bromo-5-trifluoromethyl
40 R = 4-chloro

41 R = 3-bromo-5-trifluoromethyl
42 R = 4-chloro

As shown in Reaction Scheme 16, the compound 9 prepared in Reaction Scheme 6 are reacted with commercial compounds 24 or 40 in the presence of nitrobenzene to prepare compounds 41 or 42 (L. Garuti et. al., I L Farmaco, 2004, 59, 663).

[Reaction Scheme 17]

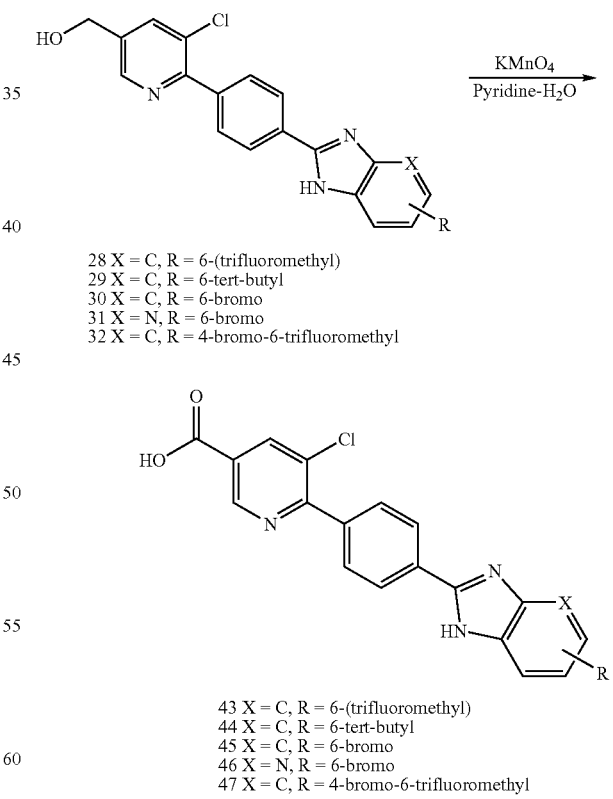

28 X = C, R = 6-(trifluoromethyl)
29 X = C, R = 6-tert-butyl
30 X = C, R = 6-bromo
31 X = N, R = 6-bromo
32 X = C, R = 4-bromo-6-trifluoromethyl 43 X = C, R = 6-(trifluoromethyl)
44 X = C, R = 6-tert-butyl
45 X = C, R = 6-bromo
46 X = N, R = 6-bromo
47 X = C, R = 4-bromo-6-trifluoromethyl As shown in Reaction Scheme 17, the compounds 28 to 32 prepared in Reaction Scheme 13 are subjected to oxidation reaction with potassium permanganate to prepare compounds 43 to 47.

[Reaction Scheme 18]

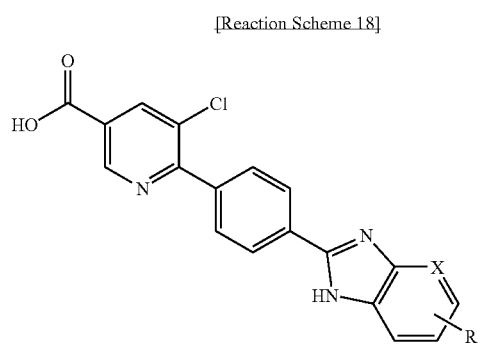

43 X = C, R = 6-(trifluoromethyl)
44 X = C, R = 6-tert-butyl
45 X = C, R = 6-bromo
46 X = N, R = 6-bromo
47 X = C, R = 4-bromo-6-trifluoromethyl H₂SO₄, MeOH →

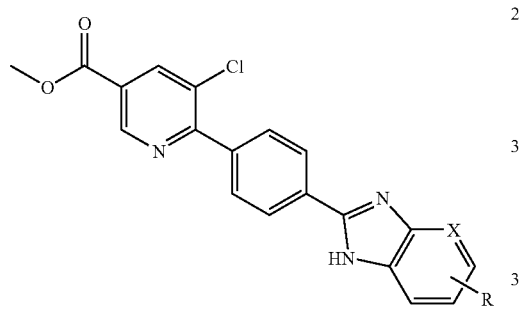

48 X = C, R = 6-(trifluoromethyl)
49 X = C, R = 6-tert-butyl
50 X = C, R = 6-bromo
51 X = N, R = 6-bromo
52 X = C, R = 4-bromo-6-trifluoromethyl As shown in Reaction Scheme 11, the compounds 43 to 47 prepared in Reaction Scheme 17 are reacted in the presence of an acid catalyst and methanol to prepare compounds 48 to 52.

[Reaction Scheme 19]

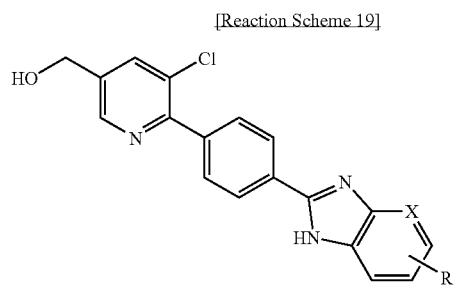

28 X = C, R = 6-(trifluoromethyl)
29 X = C, R = 6-tert-butyl
30 X = C, R = 6-bromo
31 X = N, R = 6-bromo
32 X = C, R = 4-bromo-6-trifluoromethyl Acetic anhydride →

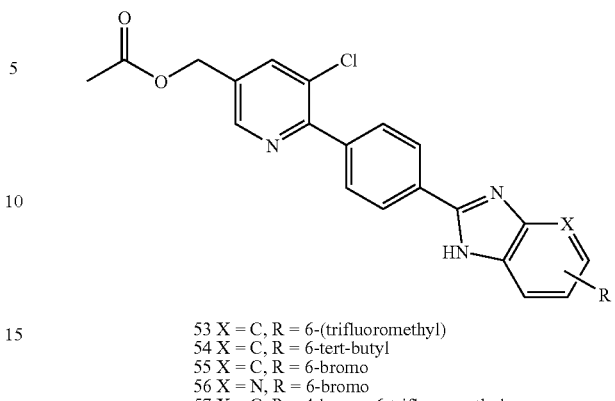

53 X = C, R = 6-(trifluoromethyl)
54 X = C, R = 6-tert-butyl
55 X = C, R = 6-bromo
56 X = N, R = 6-bromo
57 X = C, R = 4-bromo-6-trifluoromethyl As shown in Reaction Scheme 19, the compounds 28 to 32 prepared in Reaction Scheme 13 are reacted with acetic anhydride to prepare compounds 53 to 57.

[Reaction Scheme 20]

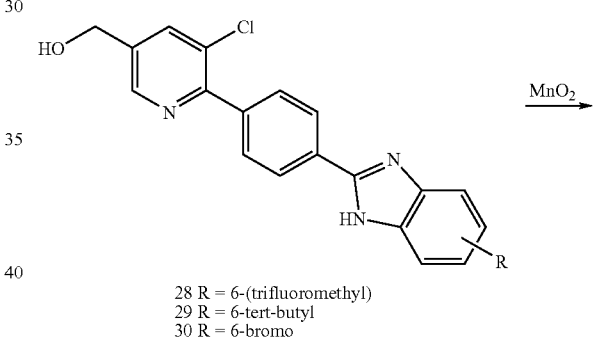

28 R = 6-(trifluoromethyl)
29 R = 6-tert-butyl
30 R = 6-bromo

MnO₂ →

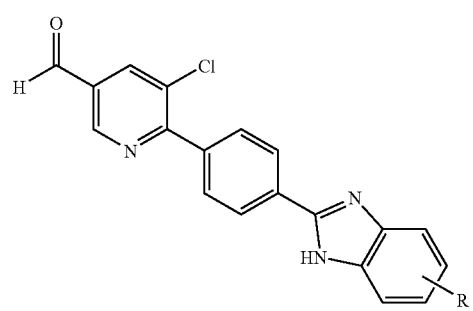

58 R = 6-(trifluoromethyl)
59 R = 6-tert-butyl
60 R = 6-bromo

As shown in Reaction Scheme 20, the compounds 28 to 32 prepared in Reaction Scheme 13 are subjected to oxidation reaction with MnO₂ to prepare compounds 58 to 60.

[Reaction Scheme 21]

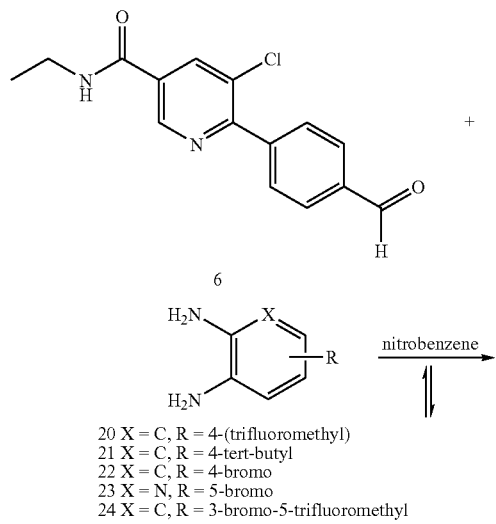

20 X = C, R = 4-(trifluoromethyl)
21 X = C, R = 4-tert-butyl
22 X = C, R = 4-bromo
23 X = N, R = 5-bromo
24 X = C, R = 3-bromo-5-trifluoromethyl 61 X = C, R = 6-(trifluoromethyl)
62 X = C, R = 6-tert-butyl
63 X = C, R = 6-bromo
64 X = N, R = 6-bromo
65 X = C, R = 4-bromo-6-trifluoromethyl As shown in Reaction Scheme 21, the compound 6 prepared in Reaction Scheme 3 and commercial compounds 20 to 24 are subjected to condensation reaction in the presence of nitrobenzene to prepare compounds 61 to 65.

[Reaction Scheme 22]

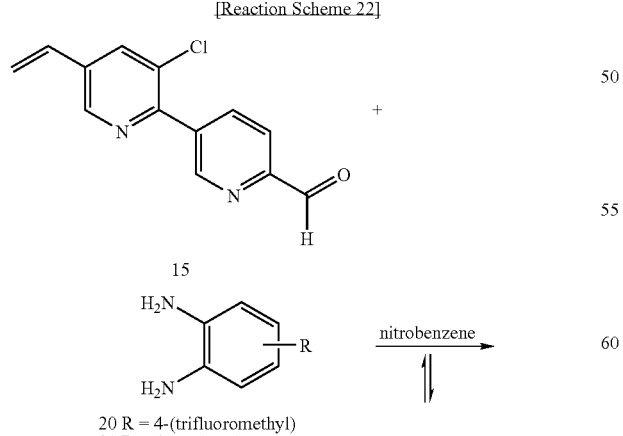

20 R = 4-(trifluoromethyl)
21 R = 4-tert-butyl
22 R = 4-bromo
23 R = 4-chloro
24 R = 3-bromo-5-trifluoromethyl

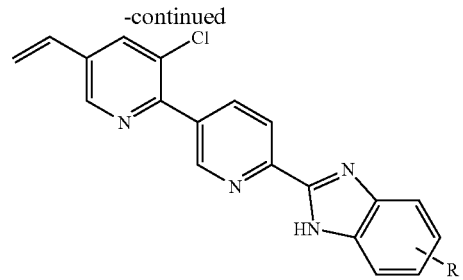

66 R = 6-(trifluoromethyl)
67 R = 6-tert-butyl
68 R = 6-bromo
69 R = 6-chloro
70 R = 4-bromo-6-trifluoromethyl As shown in Reaction Scheme 22, the compound 15 prepared in Reaction Scheme 11 and commercial compounds 20 to 24 are subjected to condensation reaction in the presence of nitrobenzene to prepare compounds 66 to 70 (L. Garuti. et. al., I L Farmaco, 2004, 59, 663).

[Reaction Scheme 23]

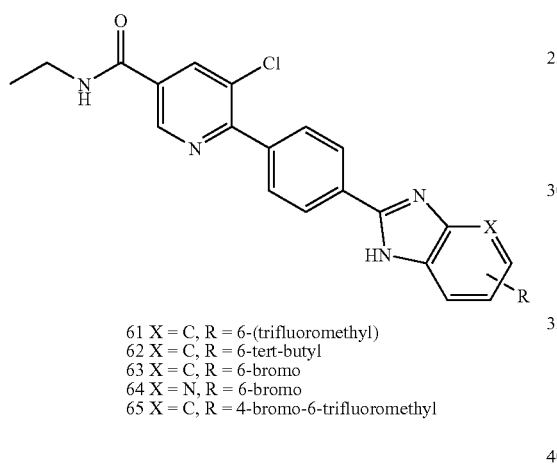

18 X = C, R = 4-morpholino
19 X = C, R = 4-(4-methylpiperazin-1-yl)
20 X = C, R = 4-(trifluoromethyl)
21 X = C, R = 4-tert-butyl
22 X = C, R = 4-bromo
23 X = N, R = 5-bromo
24 X = C, R = 3-bromo-5-trifluoromethyl
25 X = C, R = 3,5-dibromo

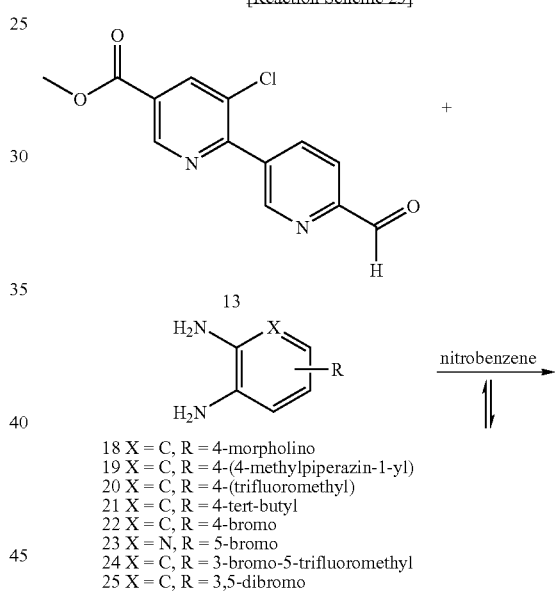

71 X = C, R = 6-morpholino
72 X = C, R = 6-(4-methylpiperazin-1-yl)
73 X = C, R = 6-(trifluoromethyl)
74 X = C, R = 6-tert-butyl
75 X = C, R = 6-bromo
76 X = N, R = 6-bromo
77 X = C, R = 4-bromo-6-trifluoromethyl
78 X = C, R = 4,6-dibromo As shown in Reaction Scheme 23, the compound 13 prepared in Reaction Scheme 9, the compounds 18 and 19 prepared in Reaction Scheme 12, and commercial compounds 20 to 25 are subjected to condensation reaction in the presence of nitrobenzene to prepare compounds 71 to 78.

[Reaction Scheme 24]

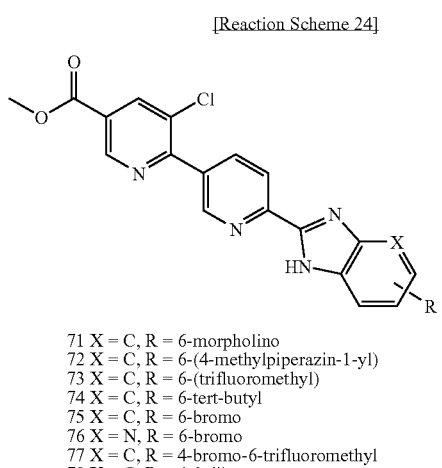

71 X = C, R = 6-morpholino
72 X = C, R = 6-(4-methylpiperazin-1-yl)
73 X = C, R = 6-(trifluoromethyl)
74 X = C, R = 6-tert-butyl
75 X = C, R = 6-bromo
76 X = N, R = 6-bromo
77 X = C, R = 4-bromo-6-trifluoromethyl
78 X = C, R = 4,6-dibromo

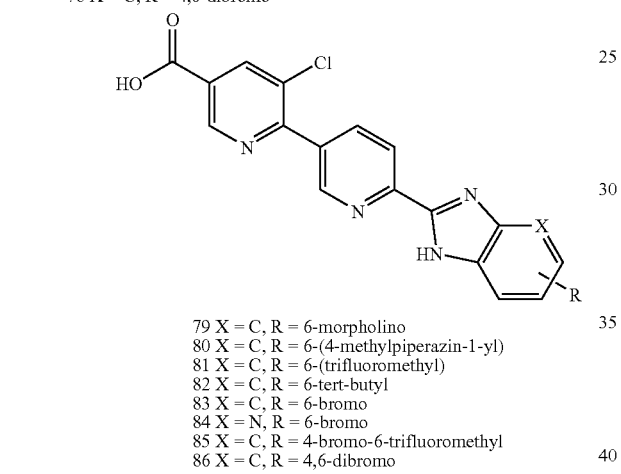

79 X = C, R = 6-morpholino
80 X = C, R = 6-(4-methylpiperazin-1-yl)
81 X = C, R = 6-(trifluoromethyl)
82 X = C, R = 6-tert-butyl
83 X = C, R = 6-bromo
84 X = N, R = 6-bromo
85 X = C, R = 4-bromo-6-trifluoromethyl
86 X = C, R = 4,6-dibromo As shown in Reaction Scheme 24, the compounds 71 to 78 prepared in Reaction Scheme 23 are reacted with lithium hydroxide to prepare compounds 79 to 86.

[Reaction Scheme 25]

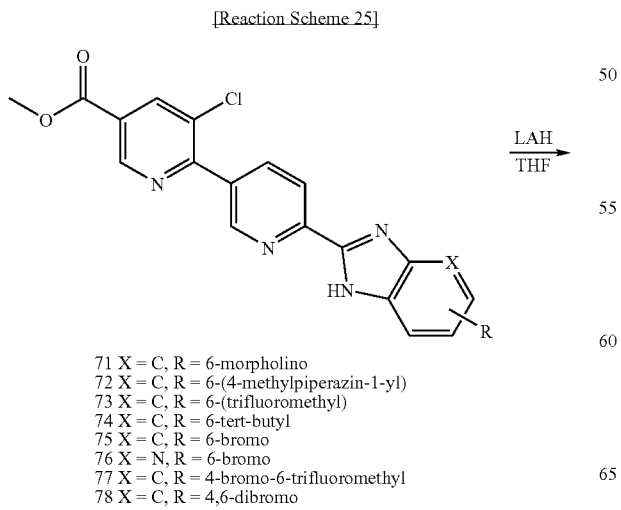

71 X = C, R = 6-morpholino
72 X = C, R = 6-(4-methylpiperazin-1-yl)
73 X = C, R = 6-(trifluoromethyl)
74 X = C, R = 6-tert-butyl
75 X = C, R = 6-bromo
76 X = N, R = 6-bromo
77 X = C, R = 4-bromo-6-trifluoromethyl
78 X = C, R = 4,6-dibromo -continued

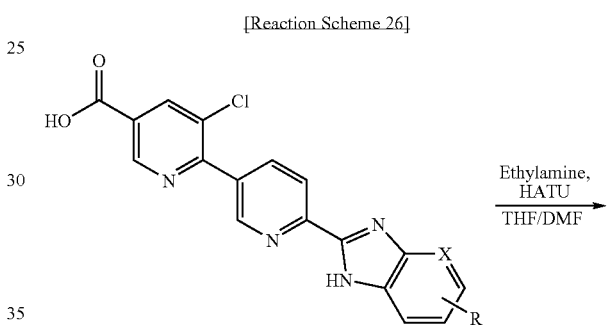

87 X = C, R = 6-morpholino
88 X = C, R = 6-(4-methylpiperazin-1-yl)
89 X = C, R = 6-(trifluoromethyl)
90 X = C, R = 6-tert-butyl
91 X = C, R = 6-bromo
92 X = N, R = 6-bromo
93 X = C, R = 4-bromo-6-trifluoromethyl
94 X = C, R = 4,6-dibromo As shown in Reaction Scheme 25, the compounds 71 to 78 prepared in Reaction Scheme 23 are reacted with lithium aluminum hydride to prepare compounds 87 to 94.

[Reaction Scheme 26]

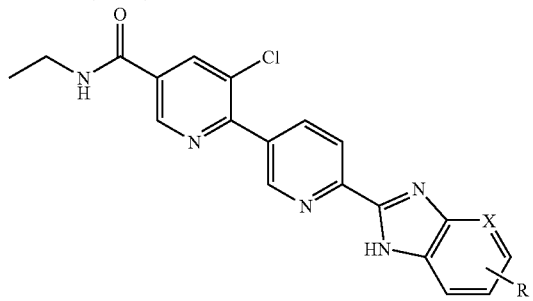

79 X = C, R = 6-morpholino
80 X = C, R = 6-(4-methylpiperazin-1-yl)
81 X = C, R = 6-(trifluoromethyl)
82 X = C, R = 6-tert-butyl
83 X = C, R = 6-bromo
84 X = N, R = 6-bromo
85 X = C, R = 4-bromo-6-trifluoromethyl
86 X = C, R = 4,6-dibromo 95 X = C, R = 6-morpholino
96 X = C, R = 6-(4-methylpiperazin-1-yl)
97 X = C, R = 6-(trifluoromethyl)
98 X = C, R = 6-tert-butyl
99 X = C, R = 6-bromo
100 X = N, R = 6-bromo
101 X = C, R = 4-bromo-6-trifluoromethyl
102 X = C, R = 4,6-dibromo As shown in Reaction Scheme 26, the compounds 79 to 86 prepared in Reaction Scheme 24 are reacted with amine to prepare compounds 95 to 102.

In still another embodiment, the present invention provides a vanilloid receptor antagonist composition comprising the biaryl benzoimidazole derivative of Formula 1, the pharmaceutically acceptable salt, solvate, or isomer thereof.

Further, the present invention provides a pharmaceutical composition comprising the biaryl benzoimidazole derivative of Formula 1, or the pharmaceutically acceptable salt, solvate, or isomer thereof.

The biaryl benzoimidazole derivative of Formula 1, or the pharmaceutically acceptable salt, solvate, or isomer thereof has excellent inhibitory effect on calcium influx in HEK cells, which show a powerful antagonistic effect on a vanilloid receptor, and has an excellent analgesic effect, thereby being used for treating or preventing a certain disorder as described below, or for treating pain related thereto.

Examples of the disorder include pain, acute pain, chronic pain, neuropathic pain, postoperative pain, migraine, arthralgia, neuropathies, nerve injury, diabetic neuropathy, neurological illness, neurodermatitis, stroke, bladder hypersensitivity, irritable bowel syndrome, a respiratory disorder such as cough, asthma, and chronic obstructive pulmonary disease, burning, psoriasis, itching, vomiting, irritation of the skin, eyes, and mucous membranes, gastric-duodenal ulcers, inflammatory intestinal diseases, and inflammatory disease.

The present invention further provides a method for preventing or treating a disorder, in which the method has an effective antagonistic effect on a vanilloid receptor, and comprises a step of administering a therapeutically effective amount of the compound of Formula 1, or the pharmaceutically acceptable salt, solvate, or isomer thereof to a mammal including human.

In order to apply the compound of the invention as a therapeutic treatment, the compounds should be formulated as a pharmaceutical composition according to conventional pharmaceutical standard methods. For example, the compounds of the invention can be dissolved in oil, propyleneglycol, or other solvents which is conventionally used in the preparation of an injectable solution. The preferred carrier is, but is not limited to, saline solution, polyethyleneglycol, ethanol, vegetable oil, isopropylmyristate or the like. For topical application, the compound of the invention can be formulated as an ointment or cream.

Hereinafter, a formulation method and an excipient are described, but are not limited thereto. The compounds of the invention can be administered in the form of a pharmaceutically acceptable salt, solvate, or isomer, and also administered alone, or together with other pharmaceutically active compounds, as well as with a suitable combination thereof.

The compound of the invention can be dissolved, suspended, or emulsified in an aqueous solution such as general saline solution and 5% dextrose, or a non-aqueous solution such as synthetic fatty acid glyceride, higher fatty acid ester, and propyleneglycol, to be formulated as injection. The formulation of the invention may contain a conventional additive such as a solubilizer, an isotonic agent, a suspending agent, an emulsifier, a stabilizer, and a preservative.

The preferred administration amount of the compound of the invention varies depending on health condition and body weight of a patient, severity of the disease, formulation of a drug, and administration route and period, but can be suitably determined by those skilled in the art. However, in order to obtain the preferred effect, the compound of the invention is administered at a daily dosage of 0.0001 to 100 mg/kg (body weight), preferably 0.001 to 100 mg/kg (body weight) one time or several times.

According to the administration method, the composition of the invention may contain 0.001 to 99% by weight, preferably 0.01 to 60% by weight of the compound of Formula 1.

The pharmaceutical composition of the invention can be administered to a mammal including rat, mouse, domestic animal, and human via various routes. All of the administration route can be employed, for example, administered orally, rectally, intravenously, intramuscularly, subcutaneously, intravaginally, or intracerbroventricularly.

Mode for the Invention

Hereinafter, the present invention will be described in detail with reference to Examples and Experimental Examples. However, these Examples and Experimental Examples are for illustrative purposes only, and the invention is not intended to be limited thereto.

EXAMPLE 1

Preparation of 4-(3-chloro-5-(hydroxymethyl)pyridin-2-yl)benzaldehyde (3)

2.68 g of sodium carbonate (25.3 mmol), 1.15 g of 4-formylphenylboronic acid (7.66 mmol), and 0.27 g of $Pd(PPh_3)_4$ were added to 1.5 g of (5,6-dichloropyridin-3-yl) methanol (8.43 mmol) dissolved in 30 mL of 1,2-dimethoxyethane and 30 mL of distilled water, and refluxed under heating and stirring for 18 hours. The mixture was cooled to room temperature, and concentrated under about 50% reduced pressure to extract the aqueous layer with ethyl acetate. The organic layer was dried over magnesium sulfate, and concentrated under reduced pressure. The residue was separated by column chromatography (eluting solvent:chloroform/methanol=10/1) to obtain 1.40 g of 4-(3-chloro-5-(hydroxymethyl)pyridin-2-yl)benzaldehyde (yield 74%).

$^1$H NMR ($CD_3OD$) δ: 10.08 (s, 1H), 8.57 (d, 1H), 8.03 (d, 2H), 8.00 (d, 1H), 7.86 (d, 2H), 4.72 (s, 2H)

EXAMPLE 2

Preparation of 5,6-dichloro-N-ethyl-nicotinamide (5)

2.0 g of O-(7-azabenzotriazol-1-yl)-N,N,N',N'-tetramethyluronium hexafluorophosphine (5.2 mmol) were added to 1.0 g of 5,6-dichloronicotinic acid (5.2 mmol) dissolved in 2.4 mL of tetrahydrofuran and 2.5 mL of dimethylformamide, and stirred at room temperature for 10 minutes. 2.6 mL of ethylamine in 2.0 M tetrahydrofuran solution (5.2 mmol) was added thereto, and refluxed under heating and stirring for 18 hours. The mixture was cooled to room temperature, concentrated under reduced pressure to be dissolved in ethyl acetate, and washed with water. The organic layer was dried over magnesium sulfate, and concentrated under reduced pressure. The residue was separated by column chromatography (eluting solvent: chloroform/methanol=20/1) to obtain 0.8 g of 5,6-dichloro-N-ethyl-nicotinamide (yield 70%).

$^1$H NMR ($CDCl_3$) δ: 8.61 (d, 1H), 8.19 (d, 1H), 6.49 (br, 1H), 3.45-3.57 (m, 2H), 1.22-1.28 (m, 3H)

EXAMPLE 3

Preparation of 5-chloro-N-ethyl-6-(4-formyl-phenyl)-nicotinamide (6)

2.44 g of $Na_2CO_3$ (23.0 mmol), 1.15 g of 4-formylphenylboronic acid (7.67 mmol), and 0.21 g of $Pd(PPh_3)_4$ were added to 1.68 g of 5,6-dichloro-N-ethyl-nicotinamide (5) (7.67 mmol) prepared in Example 2 dissolved in 30 mL of 1,2-dimethoxyethane and 30 mL of distilled water, and refluxed under heating and stirring for 18 hours. The mixture was cooled to room temperature, concentrated about 50% under reduced pressure to extract the aqueous layer with ethyl acetate. The organic layer was dried over magnesium sulfate, and concentrated under reduced pressure. The residue was separated by column chromatography (eluting solvent: chloroform/methanol=10/1) to obtain 5-chloro-N-ethyl-6-(4-formyl-phenyl)-nicotinamide 1.78 g (yield 80%).

$^1$H NMR (CDCl$_3$) δ: 10.10 (s, 1H), 8.93 (d, 1H), 8.26 (d, 1H), 8.00 (dd, 2H), 7.92 (dd, 2H), 6.30 (br, 1H), 3.51-3.60 (m, 2H), 1.25-1.32 (m, 3H)

EXAMPLE 4

Preparation of 5-(bromomethyl)-2,3-dichloropyridine (7)

3.0 mL of tribromophosphine was added to 3.0 g of (5,6-dichloropyridin-3-yl)methanol (16.9 mmol) dissolved in 60 mL of dichloromethane, and stirred at room temperature for 2 hours. 30 mL of water was added dropwise thereto, and the organic layer was separated. The organic layer was washed with saturated sodium bicarbonate, and dried over magnesium sulfate. Then, the organic layer was concentrated under reduced pressure to obtain 3.66 g of 5-(bromomethyl)-2,3-dichloropyridine (yield 90%).

$^1$H NMR (CDCl$_3$) δ: 8.31 (s, 1H), 7.83 (s, 1H), 4.41 (s, 2H)

EXAMPLE 5

Preparation of 2,3-dichloro-5-vinylpyridine (8)

2.9 g of triphenylphosphine was added to 3.6 g of compound (7) (14.9 mmol) prepared in Example 4 dissolved in 20 mL of chloroform and the mixture was reacted at 120° C. for 10 minutes by radiating with microwave radiation. And the mixture concentrated under reduced pressure to remove chloroform, and then crystallized from diethyl ether. The crystal was added to 5 mL of 40% formaldehyde, and 50% NaOH was slowly added dropwise to be a concentration of 1.7 N. After stirring for 2 hours, the resultant was extracted with ether, and concentrated under reduced pressure. The residue was separated by column chromatography (eluting solvent: chloroform/methanol=30/1) to obtain 2.5 g of 2,3-dichloro-5-vinylpyridine (yield 97%).

$^1$H NMR (CDCl$_3$) δ: 8.29 (s, 1H), 7.81 (s, 1H), 6.69-6.59 (m, 1H), 5.85 (d, 1H), 5.50 (d, 1H)

EXAMPLE 6

Preparation of 4-(3-chloro-5-vinylpyridin-2-yl)benzaldehyde (9)

4.1 g of Na$_2$CO$_3$ (39 mmol), 2.0 g of 4-formylphenylboronic acid (13 mmol), and 0.45 g of Pd(PPh$_3$)$_4$ were added to 2.5 g of compound (8) (14.9 mmol) prepared in Example 5 dissolved in 50 mL of 1,2-dimethoxyethane and 50 mL of distilled water, and refluxed under heating and stirring for 18 hours. The mixture was cooled to room temperature, and concentrated about 50% under reduced pressure. The aqueous layer was extracted with ethyl acetate, the organic layer was dried over magnesium sulfate, and then concentrated under reduced pressure. The residue was separated by column chromatography (eluting solvent: ethyl acetate/hexane=1/4) to obtain 3.0 g 4-(3-chloro-5-vinylpyridin-2-yl)benzaldehyde (yield 82%).

$^1$H NMR (CDCl$_3$) δ: 10.10 (s, 1H), 8.61 (s, 1H), 8.00-7.91 (m, 4H), 7.87 (s, 1H), 6.78-6.68 (m, 1H), 5.93 (d, 1H), 5.52 (d, 1H)

EXAMPLE 7

Preparation of 5,6-dichloro-nicotinic acid methyl ester (10)

4.45 mL of sulfuric acid was added to 5.0 g of 5,6-dichloronicotinic acid (26 mmol) dissolved in 50 mL of methanol, and refluxed under heating and stirring for 18 hours. The mixture was cooled to 4° C., neutralized with a saturated sodium bicarbonate solution, and methanol was concentrated under reduced pressure. The aqueous layer was extracted with ethyl acetate, and the organic layer was separated to be dried over magnesium sulfate, and concentrated under reduced pressure. The residue was separated by column chromatography (eluting solvent: chloroform/methanol=20/1) to obtain 5.2 g of white solid, 5,6-dichloro-nicotinic acid methyl ester (yield 97%).

$^1$H NMR (CDCl$_3$) δ: 8.86 (s, 1H), 8.34 (s, 1H), 3.96 (s, 3H)

EXAMPLE 8

Preparation of 3-chloro-6'-methyl-[2,3']bipyridyl-5-carboxylic acid methyl ester (12)

0.29 of Na$_2$CO$_3$ (0.273 mmol), 0.25 g of 6-methylpyridin-3-ylboronic acid (11) (0.18 mmol) and 0.11 g of Pd(PPh$_3$)$_4$ were added to 0.4 g of 5,6-dichloro-nicotinic acid methyl ester (10) (0.2 mmol) prepared in Example 7 dissolved in 14 mL of 1,2-dimethoxyethane and 7 mL of distilled water, and refluxed under heating and stirring for 18 hours. The mixture was cooled to room temperature, and concentrated about 50% under reduced pressure. The aqueous layer was extracted with ethyl acetate, and the organic layer was dried over magnesium sulfate, concentrated under reduced pressure. The residue was separated by column chromatography (eluting solvent: chloroform/methanol=10/1) to obtain 0.42 g of 3-chloro-6'-methyl-[2,3']bipyridyl-5-carboxylic acid methyl ester (yield 88%).

$^1$H NMR (CDCl$_3$) δ: 9.16 (d, 1H), 8.96 (s, 1H), 8.40 (d, 1H), 8.03 (dd, 1H), 7.29 (d, 1H), 4.00 (s, 3H), 2.65 (S, 3H)

EXAMPLE 9

Preparation of 3-chloro-6'-formyl-[2,3']bipyridyl-5-carboxylic acid methyl ester (13)

0.6 g of 3-chloro-6'-methyl-[2,3']bipyridyl-5-carboxylic acid methyl ester (12) (2.3 mmol) prepared in Example 8 was dissolved in 10 mL of 1,4-dioxane, and 0.75 g of selenium dioxide (6.9 mmol) was added thereto. The mixture was refluxed under heating and stirring for 18 hours, and cooled to room temperature. The mixture was concentrated under reduced pressure, and then dissolved in ethyl acetate to be washed with water. The organic layer was dried over magnesium sulfate, and concentrated under reduced pressure. The residue was separated by column chromatography (eluting solvent: chloroform/methanol=10/1) to obtain 0.51 g of yellow crystal, 3-chloro-6'-formyl-[2,3']bipyridyl-5-carboxylic acid methyl ester (yield 81%)

$^1$H NMR (CDCl$_3$) δ: 10.04 (s, 1H), 9.14 (m, 2H), 8.50 (s, 1H), 8.07 (d, 1H), 3.92 (S, 3H)

EXAMPLE 10

Preparation of 3-chloro-6'-methyl-5-vinyl-2,3'-bipyridine (14)

8.1 g of Na$_2$CO$_3$ (76 mmol), 3.5 g of 6-methylpyridin-3-ylboronic acid (11) (25 mmol), and 0.97 g of Pd(PPh$_3$)$_4$ were added to 4.9 g of compound (8) (28 mmol) prepared in Example 5 dissolved in 100 mL of 1,2-dimethoxyethane and 100 mL of distilled water, and refluxed under heating and stirring for 18 hours. The mixture was cooled to room temperature, and concentrated about 50% under reduced pressure. The aqueous layer was extracted with ethyl acetate, and the organic layer was dried over magnesium sulfate, concentrated under reduced pressure. The residue was separated by column chromatography (eluting solvent: ethyl acetate/hexane=1/4) to obtain 5.2 g of 3-chloro-6'-methyl-5-vinyl-2,3'-bipyridine (yield 90%).

$^1$H NMR (CDCl$_3$) δ: 8.92 (s, 1H), 8.59 (s, 1H), 7.99 (d, 1H), 7.84 (s, 1H), 7.28 (s, 1H), 6.76-6.66 (m, 1H), 5.91 (d, 1H), 5.50 (d, 1H), 2.64 (s, 3H)

EXAMPLE 11

Preparation of 3-chloro-5-vinyl-2,3'-bipyridine-6'-carbaldehyde (15)

4.0 g of 3-chloro-6'-methyl-5-vinyl-2,3'-bipyridine (14) (17.3 mmol) prepared in Example 10 was dissolved in 50 mL of 1,4-dioxane, and 5.8 g of selenium dioxide (52 mmol) was added thereto. The mixture was refluxed under heating and stirring for 18 hours, and cooled to room temperature. Then, the mixture was concentrated under reduced pressure, and dissolved in ethyl acetate to be washed with water. The organic layer was dried over magnesium sulfate, and concentrated under reduced pressure. The residue was separated by column chromatography (eluting solvent:ethyl acetate/hexane=1/4) to obtain 3.2 g of 3-chloro-5-vinyl-2,3'-bipyridine-6'-carbaldehyde (yield 75%).

$^1$H NMR (CDCl$_3$) δ: 10.14 (s, 1H), 9.18 (s, 1H), 8.63 (s, 1H), 8.28 (d, 1H), 8.05 (d, 1H), 7.87 (s, 1H), 6.77-6.67 (m, 1H), 5.95 (d, 1H), 5.53 (d, 1H)

EXAMPLE 12

Preparation of 4-morpholinobenzene-1,2-diamine (18)

0.1 g of 10% Pd/C was added to 1.0 g of 5-morpholin-4-yl-2-nitro-phenylamine (4.3 mmol) dissolved in 43 mL of methanol, and allowed to stir under hydrogen balloon at room temperature for 4 hours. The mixture was filtered with diatomaceous earth to remove the catalyst, and concentrated under reduced pressure to obtain 0.9 g of 4-morpholinobenzene-1,2-diamine (yield 100%).

$^1$H NMR (CDCl$_3$) δ: 6.64 (d, 1H), 6.34 (d, 1H), 6.30 (dd, 1H), 3.84 (t, 4H), 3.43 (br, 2H), 3.23 (br, 2H), 3.01 (t, 4H)

EXAMPLE 13

Preparation of 4-(4-methyl-piperazin-1-yl)-benzene-1,2-diamine (19)

0.9 g of 4-(4-methyl-piperazin-1-yl)-benzene-1,2-diamine (yield 97%) was obtained in the same manner as Example 12, except that 5-(4-methyl-piperazin-1-yl)-2-nitro-phenylamine was used instead of 5-morpholin-4-yl-2-nitro-phenylamine in Example 12.

$^1$H NMR (CDCl$_3$) δ: 6.65 (d, 1H), 6.47 (br, 1H), 6.31 (d, 1H), 3.09-2.98 (m, 4H), 2.61-2.55 (m, 4H), 2.31 (s, 3H)

EXAMPLE 14

Preparation of {5-chloro-6-[4-(6-morpholin-4-yl-1H-benzoimidazol-2-yl)-phenyl]-pyridin-3-yl}-methanol (26)

0.50 g of 4-(3-chloro-5-(hydroxymethyl)pyridin-2-yl)benzaldehyde (3) (2.02 mmol) prepared in Example 1 and 0.39 g of 4-morpholinobenzene-1,2-diamine (18) (2.02 mmol) prepared in Example 12 were dissolved in nitrobenzene (5.5 mL), and refluxed under heating for 2 hours. The mixture was cooled to room temperature, and concentrated under reduced pressure. The residue was separated by column chromatography (eluting solvent: chloroform/methanol=10/1) to obtain 0.68 g of {5-chloro-6-[4-(6-morpholin-4-yl-1H-benzoimidazol-2-yl)-phenyl]-pyridin-3-yl}-methanol (yield 80%).

$^1$H NMR (CD$_3$OD) δ: 8.60 (d, 1H), 8.17 (d, 2H), 8.04 (d, 1H), 7.85 (d, 2H), 7.54 (d, 1H), 7.14 (d, 1H), 7.09 (dd, 1H), 5.22 (s, 2H), 3.88 (m, 4H), 3.18 (m, 4H)

EXAMPLE 15

Preparation of (5-chloro-6-{4-[6-(4-methyl-piperazin-1-yl)-1H-benzoimidazol-2-yl]-phenyl}-pyridin-3-yl)-methanol (27)

0.66 g of (5-chloro-6-{-4-[6-(4-methyl-piperazin-1-yl)-1H-benzoimidazol-2-yl]-phenyl}-pyridin-3-yl)-methanol (yield 75%) was obtained in the same manner as Example 14, except that 4-(4-methyl-piperazin-1-yl)-benzene-1,2-diamine (19) prepared in Example 13 was used instead of 4-morpholinobenzene-1,2-diamine (18) in Example 14.

$^1$H NMR (CD$_3$OD) δ: 8.55 (d, 1H), 8.15 (d, 2H), 8.03 (d, 1H), 7.86 (d, 2H), 7.53 (d, 1H), 7.13 (s, 1H), 7.08 (dd, 1H)

EXAMPLE 16

Preparation of {5-chloro-6-[4-(6-trifluoromethyl-1H-benzoimidazol-2-yl)-phenyl]-pyridin-3-yl}-methanol (28)

0.73 g of {5-chloro-6-[4-(6-trifluoromethyl-1H-benzoimidazol-2-yl)-phenyl]-pyridin-3-yl}-methanol (yield 90%) was obtained in the same manner as Example 14, except that compound (20) was used instead of 4-morpholinobenzene-1,2-diamine(18) in Example 14.

$^1$H NMR (CD$_3$OD) δ: 8.58 (s, 1H), 8.26 (d, 2H), 8.00 (s, 1H), 7.94-7.88 (m, 3H), 7.81 (m, 3H), 7.81 (br, 1H), 7.57 (d, 1H), 4.73 (s, 2H)

EXAMPLE 17

Preparation of {6-[4-(6-tert-butyl-1H-benzoimidazol-2-yl)-phenyl]-5-chloro-pyridin-3-yl}-methanol (29)

0.75 g of {6-[4-(6-tert-butyl-1H-benzoimidazol-2-yl)-phenyl]-5-chloro-pyridin-3-yl}-methanol (yield 95%) was obtained in the same manner as Example 14, except that compound (21) was used instead of 4-morpholinobenzene-1, 2-diamine(18) in Example 14.

¹H NMR (CD₃OD) δ: 8.56 (d, 1H), 8.20 (dd, 2H), 8.00 (d, 1H), 7.86 (dd, 2H), 7.63 (br, 1H), 7.56 (br, 1H), 7.40 (dd, 1H), 4.73 (s, 2H), 1.42 (s, 9H)

EXAMPLE 18

Preparation of {6-[4-(6-bromo-1H-benzoimidazol-2-yl)-phenyl]-5-chloro-pyridin-3-yl}-methanol (30)

0.71 g of {6-[4-(6-bromo-1H-benzoimidazol-2-yl)-phenyl]-5-chloro-pyridin-3-yl}-methanol (yield 85%) was obtained in the same manner as Example 14, except that compound (22) was used instead of 4-morpholinobenzene-1,2-diamine(18) in Example 14.

¹H NMR (CD₃OD) δ: 8.57 (d, 1H), 8.20 (dd, 2H), 8.00 (d, 1H), 7.87 (dd, 2H), 7.76 (br, 1H), 7.50 (br, 1H), 7.41 (dd, 1H), 4.73 (s, 2H)

EXAMPLE 19

Preparation of {6-[4-(6-bromo-1H-imidazo[4,5-b]pyridin-2-yl)-phenyl]-5-chloro-pyridin-3-yl}-methanol (31)

0.59 g of {6-[4-(6-bromo-1H-imidazo[4,5-b]pyridin-2-yl)-phenyl]-5-chloro-pyridin-3-yl}-methanol (yield 70%) was obtained in the same manner as Example 14, except that compound (23) was used instead of 4-morpholinobenzene-1,2-diamine(18) in Example 14.

¹H NMR (CD₃OD) δ: 8.57 (s, 1H), 8.11 (d, 2H), 8.01 (s, 1H), 7.97 (s, 1H), 7.87-7.80 (m, 3H), 4.73 (s, 2H)

EXAMPLE 20

Preparation of {6-[4-(4-bromo-6-trifluoromethyl-1H-benzoimidazol-2-yl)-phenyl]-5-chloro-pyridin-3-yl}-methanol (32)

0.83 g of {6-[4-(4-bromo-6-trifluoromethyl-1H-benzoimidazol-2-yl)-phenyl]-5-chloro-pyridin-3-yl}-methanol (yield 85%) was obtained in the same manner as Example 14, except that compound (24) was used instead of 4-morpholinobenzene-1,2-diamine(18) in Example 14.

¹H NMR (CD₃OD) δ: 8.58 (s, 2H), 8.32 (d, 2H), 8.01 (s, 1H), 7.91 (d, 2H), 7.73 (s, 1H), 4.73 (s, 2H)

EXAMPLE 21

Preparation of {5-chloro-6-[4-(4,6-dibromo-1H-benzoimidazol-2-yl)-phenyl]-pyridin-3-yl}-methanol (33)

0.75 g of {5-chloro-6-[4-(4,6-dibromo-1H-benzoimidazol-2-yl)-phenyl]-pyridin-3-yl}-methanol (yield 75%) was obtained in the same manner as Example 14, except that compound (25) was used instead of 4-morpholinobenzene-1,2-diamine(18) in Example 14.

¹H NMR (CD₃OD) δ: 8.56 (s, 1H), 8.23 (d, 2H), 7.99 (s, 1H), 7.85 (d, 2H), 7.71 (br, 1H), 7.56 (s, 1H), 4.73 (s, 2H)

EXAMPLE 22

Preparation of 2-[4-(5-bromomethyl-3-chloro-pyridin-2-yl)-phenyl]-6-trifluoromethyl-1H-benzoimidazole (34)

3.2 g of 2-[4-(5-bromomethyl-3-chloro-pyridin-2-yl)-phenyl]-6-trifluoromethyl-1H-benzoimidazole (yield 93%) was obtained in the same manner as Example 4, except that 3.0 g of the compound (28) (7.4 mmol) prepared in Example 16 was used instead of (5,6-dichloropyridin-3-yl)methanol in Example 4.

¹H NMR (CDCl₃) δ: 8.61 (s, 1H), 8.19 (d, 2H), 7.95 (s, 1H), 7.83-7.78 (m, 3H), 7.72 (d, 1H), 7.51 (d, 1H), 4.49 (s, 2H)

EXAMPLE 23

Preparation of 2-[4-(5-bromomethyl-3-chloro-pyridin-2-yl)-phenyl]-6-tert-butyl-1H-benzoimidazole (35)

2.9 g of 2-[4-(5-bromomethyl-3-chloro-pyridin-2-yl)-phenyl]-6-tert-butyl-1H-benzoimidazole (yield 86%) was obtained in the same manner as Example 4, except that compound (29) prepared in Example 17 was used instead of (5,6-dichloropyridin-3-yl)methanol in Example 4.

¹H NMR (CD₃OD) δ: 8.57 (s, 1H), 8.32 (d, 2H), 7.80-7.61 (m, 3H), 7.50 (d, 2H), 7.30 (m, 1H), 4.46 (s, 1H), 1.23 (s, 9H)

EXAMPLE 24

Preparation of 6-bromo-2-[4-(5-bromomethyl-3-chloro-pyridin-2-yl)-phenyl]-1H-benzoimidazole (36)

3.2 g of 6-bromo-2-[4-(5-bromomethyl-3-chloro-pyridin-2-yl)-phenyl]-1H-benzoimidazole (yield 89%) was obtained in the same manner as Example 4, except that compound (30) prepared in Example 18 was used instead of (5,6-dichloropyridin-3-yl)methanol in Example 4.

¹H NMR (CD₃OD) δ: 8.60 (s, 1H), 8.17 (d, 2H), 7.90 (s, 1H), 7.80-7.76 (m, 3H), 7.69 (d, 1H), 7.48 (d, 1H), 4.45 (s, 2H)

EXAMPLE 25

Preparation of 2-[4-(3-chloro-5-vinyl-pyridin-2-yl)-phenyl]-6-trifluoromethyl-1H-benzoimidazole (37)

1.6 g of 2-[4-(3-chloro-5-vinyl-pyridin-2-yl)-phenyl]-6-trifluoromethyl-1H-benzoimidazole (yield 95%) was obtained in the same manner as Example 5, except that compound (34) prepared in Example 22 was used instead of compound (7) in Example 5.

¹H NMR (CDCl₃) δ: 8.63 (s, 1H), 8.12 (d, 2H), 7.92-7.88 (m, 3H), 7.65 (m, 1H), 7.56 (m, 2H), 6.78-6.69 (m, 1H), 5.92 (d, 1H), 5.53 (d, 1H)

EXAMPLE 26

Preparation of 6-tert-butyl-2-[4-(3-chloro-5-vinyl-pyridin-2-yl)-phenyl]-1H-benzoimidazole (38)

1.5 g of 6-tert-butyl-2-[4-(3-chloro-5-vinyl-pyridin-2-yl)-phenyl]-1H-benzoimidazole (yield 90%) was obtained in the same manner as Example 5, except that compound (35) prepared in Example 23 was used instead of compound (7) in Example 5.

$^1$H NMR (CDCl$_3$) δ: 8.61 (s, 1H), 8.10 (d, 2H), 7.85-7.82 (m, 3H), 7.62 (d, 2H), 7.36 (m, 1H), 6.76-6.67 (m, 1H), 5.91 (d, 1H), 5.49 (d, 1H), 1.38 (s, 9H)

EXAMPLE 27

Preparation of 6-bromo-2-[4-(3-chloro-5-vinyl-pyridin-2-yl)-phenyl]-1H-benzoimidazole (39)

1.5 g of 6-bromo-2-[4-(3-chloro-5-vinyl-pyridin-2-yl)-phenyl]-1H-benzoimidazole (yield 87%) was obtained in the same manner as Example 5, except that compound (36) prepared in Example 24 was used instead of compound (7) in Example 5.
$^1$H NMR (CDCl$_3$) δ: 8.60 (s, 1H), 8.07 (d, 2H), 7.86-7.72 (m, 5H), 7.42 (m, 1H), 6.77-6.68 (m, 1H), 5.88 (d, 1H), 5.50 (d, 1H)

EXAMPLE 28

Preparation of 4-bromo-2-[4-(3-chloro-5-vinyl-pyridin-2-yl)-phenyl]-6-trifluoromethyl-1H-benzoimidazole (41)

0.88 g of compound (9) (0.36 mmol) prepared in Example 6 and 0.92 g of 3-bromo-5-(trifluoromethyl)benzene-1,2-diamine(24) (0.36 mmol) were dissolved in nitrobenzene (1 mL), and refluxed under heating for 2 hours. The mixture was cooled to room temperature, and concentrated under reduced pressure. The residue was separated by column chromatography (eluting solvent: chloroform/methanol=10/1) to obtain 0.26 g of 4-bromo-2-[4-(3-chloro-5-vinyl-pyridin-2-yl)-phenyl]-6-trifluoromethyl-1H-benzoimidazole (yield 72%).
$^1$H NMR (CDCl$_3$) δ: 8.65 (s, 1H), 8.05 (d, 2H), 7.89 (s, 2H), 7.79 (d, 2H), 7.69 (s, 1H), 6.78-6.69 (m, 1H), 5.94 (d, 1H), 5.53 (d, 1H)

EXAMPLE 29

Preparation of 6-chloro-2-[4-(3-chloro-5-vinyl-pyridin-2-yl)-phenyl]-1H-benzoimidazole (42)

0.29 g of 6-chloro-2-[4-(3-chloro-5-vinyl-pyridin-2-yl)-phenyl]-1H-benzoimidazole (yield 81%) was obtained in the same manner as Example 28, except that 4-chlorobenzene-1,2-diamine (40) was used instead of 3-bromo-5-(trifluoromethyl)benzene-1,2-diamine in Example 28.
$^1$H NMR (CDCl$_3$) δ: 8.62 (s, 1H), 8.02 (d, 2H), 7.87 (s, 1H), 7.79 (d, 2H), 7.55-7.51 (brs, 2H), 7.24 (d, 1H), 6.78-6.68 (m, 1H), 5.93 (d, 1H), 5.51 (d, 1H)

EXAMPLE 30

Preparation of 5-chloro-6-[4-(6-trifluoromethyl-1H-benzoimidazol-2-yl)-phenyl]-nicotinic acid (43)

0.40 g of {5-chloro-6-[4-(6-trifluoromethyl-1H-benzoimidazol-2-yl)-phenyl]-pyridin-3-yl}-methanol (28) (0.99 mmol) prepared in Example 16 was dissolved in 4 mL of pyridine and 2 mL of distilled water. 0.59 g of potassium permanganate (3.71 mmol) was added thereto, and reacted at 110° C. for 4 hours. Then, 0.59 g of potassium permanganate (3.71 mmol) and 2 mL of distilled water were added thereto, and reacted at 110° C. for 18 hours. The resultant was cooled to room temperature, and concentrated under reduced pressure. The aqueous layer was washed with ethyl acetate, pH 1 was adjusted with concentrated hydrochloric acid, and extracted with ethyl acetate several times. The organic layer was dried over magnesium sulfate, and concentrated under reduced pressure. The residue was separated by column chromatography (eluting solvent: chloroform/methanol=10/1) to obtain 0.32 g of 5-chloro-6-[4-(6-trifluoromethyl-1H-benzoimidazol-2-yl)-phenyl]-nicotinic acid (yield 77%).
$^1$H NMR (CD$_3$OD) δ: 9.09 (s, 1H), 8.40 (s, 1H), 8.20 (d, 2H), 7.87 (d, 2H), 7.66 (br, 1H), 7.56 (d, 1H), 7.42 (d, 1H)

EXAMPLE 31

Preparation of 6-[4-(6-tert-butyl-1H-benzoimidazol-2-yl)-phenyl]-5-chloro-nicotinic acid (44)

0.37 g of 6-[4-(6-tert-butyl-1H-benzoimidazol-2-yl)-phenyl]-5-chloro-nicotinic acid (yield 92%) was obtained in the same manner as Example 30, except that compound (29) prepared in Example 17 was used instead of compound (28) in Example 30.
$^1$H NMR (CD$_3$OD) δ: 9.08 (d, 1H), 8.43 (d, 1H), 8.21 (d, 2H), 7.88 (d, 2H), 7.64 (d, 1H), 7.56 (d, 1H), 7.40 (dd, 1H), 1.42 (s, 9H)

EXAMPLE 32

Preparation of 6-[4-(6-bromo-1H-benzoimidazol-2-yl)-phenyl]-5-chloro-nicotinic acid (45)

0.38 g of 6-[4-(6-bromo-1H-benzoimidazol-2-yl)-phenyl]-5-chloro-nicotinic acid (yield 89%) was obtained in the same manner as Example 30, except that compound (30) prepared in Example 18 was used instead of compound (28) in Example 30.
$^1$H NMR (CD$_3$OD) δ: 9.07 (d, 1H), 8.42 (d, 1H), 8.22 (d, 2H), 7.90 (d, 2H), 7.80 (br, 1H), 7.62 (br, 1H), 7.40 (dd, 1H)

EXAMPLE 33

Preparation of 6-[4-(6-bromo-1H-imidazo[4,5-b]pyridin-2-yl)-phenyl]-5-chloro-nicotinic acid (46)

0.32 g of 6-[4-(6-bromo-1H-imidazo[4,5-b]pyridin-2-yl)-phenyl]-5-chloro-nicotinic acid (yield 75%) was obtained in the same manner as Example 30, except that compound (31) prepared in Example 19 was used instead of compound (28) in Example 30.
$^1$H NMR (CD$_3$OD) δ: 9.07 (s, 1H), 8.55 (s, 1H), 8.43 (s, 1H), 8.01-7.98 (m, 3H), 7.77 (d, 2H)

EXAMPLE 34

Preparation of 6-[4-(4-bromo-6-trifluoromethyl-1H-benzoimidazol-2-yl)-phenyl]-5-chloro-nicotinic acid (47)

0.44 g of 6-[4-(4-bromo-6-trifluoromethyl-1H-benzoimidazol-2-yl)-phenyl]-5-chloro-nicotinic acid (yield 90%) was obtained in the same manner as Example 30, except that compound (32) prepared in Example 20 was used instead of compound (28) in Example 30.
$^1$H NMR (CD$_3$OD) δ: 9.09 (d, 1H), 8.44 (d, 1H), 8.32 (d, 2H), 7.93 (d, 2H), 7.90 (s, 1H), 7.65 (s, 1H)

EXAMPLE 35

Preparation of 5-chloro-6-[4-(6-trifluoromethyl-1H-benzoimidazol-2-yl)-phenyl]-nicotinic acid methyl ester (48)

0.18 g of 5-chloro-6-[4-(6-trifluoromethyl-1H-benzoimidazol-2-yl)-phenyl]-nicotinic acid methyl ester (yield 85%) was obtained in the same manner as Example 7, except that compound (43) prepared in Example 30 was used instead of 5,6-dichloronicotinic acid in Example 7.

$^1$H NMR (CDCl$_3$) δ: 9.19 (d, 1H), 8.44 (d, 1H), 8.18 (d, 2H), 7.98 (s, 1H), 7.96 (d, 2H), 7.74 (d, 1H), 7.56 (d, 1H)

EXAMPLE 36

Preparation of 6-[4-(6-tert-butyl-1H-benzoimidazol-2-yl)-phenyl]-5-chloro-nicotinic acid methyl ester (49)

0.18 g of 6-[4-(6-tert-butyl-1H-benzoimidazol-2-yl)-phenyl]-5-chloro-nicotinic acid methyl ester (yield 91%) was obtained in the same manner as Example 7, except that compound (44) prepared in Example 31 was used instead of 5,6-dichloronicotinic acid in Example 7.

$^1$H NMR (CD$_3$OD) δ: 9.14 (d, 1H), 8.52 (d, 1H), 8.23 (d, 2H), 7.95 (d, 2H), 7.63 (br, 2H), 7.42 (d, 1H)

EXAMPLE 37

Preparation of 6-[4-(6-bromo-1H-benzoimidazol-2-yl)-phenyl]-5-chloro-nicotinic acid methyl ester (50)

0.19 g of 6-[4-(6-bromo-1H-benzoimidazol-2-yl)-phenyl]-5-chloro-nicotinic acid methyl ester (yield 89%) was obtained in the same manner as Example 7, except that compound (45) prepared in Example 32 was used instead of 5,6-dichloronicotinic acid in Example 7.

$^1$H NMR (CD$_3$OD) δ: 9.12 (d, 1H), 8.50 (d, 1H), 8.21 (d, 2H), 7.82 (br, 1H), 7.57 (br, 1H), 7.41 (dd, 1H)

EXAMPLE 38

Preparation of 6-[4-(6-bromo-1H-imidazo[4,5-b]pyridin-2-yl)-phenyl]-5-chloro-nicotinic acid methyl ester (51)

0.16 g of 6-[4-(6-bromo-1H-imidazo[4,5-b]pyridin-2-yl)-phenyl]-5-chloro-nicotinic acid methyl ester (yield 75%) was obtained in the same manner as Example 7, except that compound (46) prepared in Example 33 was used instead of 5,6-dichloronicotinic acid in Example 7.

$^1$H NMR (CD$_3$OD) δ: 9.15 (s, 1H), 8.50 (s, 1H), 8.24 (d, 2H), 7.99 (d, 2H), 7.60 (br, 2H), 7.40 (d, 1H)

EXAMPLE 39

Preparation of 6-[4-(4-bromo-6-trifluoromethyl-1H-benzoimidazol-2-yl)-phenyl]-5-chloro-nicotinic acid methyl ester (52)

0.16 g of 6-[4-(4-bromo-6-trifluoromethyl-1H-benzoimidazol-2-yl)-phenyl]5-chloro-nicotinic acid methyl ester (yield 75%) was obtained in the same manner as Example 7, except that compound (47) prepared in Example 34 was used instead of 5,6-dichloronicotinic acid in Example 7.

$^1$H NMR (CD$_3$OD) δ: 9.13 (s, 1H), 8.51 (s, 1H), 8.30 (d, 2H), 8.00 (d, 2H), 7.91 (s, 1H), 7.74 (s, 1H), 4.00 (s, 3H)

EXAMPLE 40

Preparation of acetic acid 5-chloro-6-[4-(6-trifluoromethyl-1H-benzoimidazol-2-yl)-phenyl]-pyridin-3-yl methyl ester (53)

0.20 g of {5-chloro-6-[4-(6-trifluoromethyl-1H-benzoimidazol-2-yl)-phenyl]-pyridin-3-yl}-methanol (28) (0.50 mmol) prepared in Example 16 was added to 5 mL of acetic anhydride, and refluxed under heating and stirring for 12 hours. The mixture was cooled to room temperature, ethyl acetate was added thereto, and washed with saturated sodium bicarbonate. The organic layer was dried over magnesium sulfate, and concentrated under reduced pressure. The residue was separated by column chromatography (eluting solvent: chloroform/methanol=20/1) to obtain 0.20 g of acetic acid 5-chloro-6-[4-(6-trifluoromethyl-1H-benzoimidazol-2-yl)-phenyl]-pyridin-3-yl methyl ester (yield 90%).

$^1$H NMR (CD$_3$OD) δ: 8.62 (s, 1H), 8.25 (d, 2H), 8.06 (s, 1H), 7.95 (br, 1H), 7.87 (d, 2H), 7.36 (br, 1H), 7.57 (d, 1H), 5.23 (s, 2H), 2.14 (s, 3H)

EXAMPLE 41

Preparation of acetic acid 6-[4-(6-tert-butyl-1H-benzoimidazol-2-yl)-phenyl]-5-chloro-pyridin-3-yl methyl ester (54)

0.21 g of acetic acid 6-[4-(6-tert-butyl-1H-benzoimidazol-2-yl)-phenyl]-5-chloro-pyridin-3-yl methyl ester (yield 95%) was obtained in the same manner as Example 40, except that compound (29) prepared in Example 17 was used instead of compound (28) in Example 40.

$^1$H NMR (CD$_3$OD) δ: 8.62 (s, 1H), 8.20 (d, 2H), 8.05 (s, 1H), 7.91-7.87 (m, 3H), 7.66 (br, 1H), 7.46 (d, 1H), 5.23 (s, 2H), 2.14 (s, 3H), 1.42 (s, 9H)

EXAMPLE 42

Preparation of acetic acid 6-[4-(6-bromo-1H-benzoimidazol-2-yl)-phenyl]-5-chloro-pyridin-3-yl methyl ester (55)

0.21 g of acetic acid 6-[4-(6-bromo-1H-benzoimidazol-2-yl)-phenyl]-5-chloro-pyridin-3-yl methyl ester (yield 92%) was obtained in the same manner as Example 40, except that compound (30) prepared in Example 18 was used instead of compound (28) in Example 40.

$^1$H NMR (CDCl$_3$) δ: 8.60 (s, 1H), 8.15 (d, 2H), 8.01 (d, 1H), 7.82 (d, 2H), 7.74 (br, 1H), 7.53 (br, 1H), 7.38 (d, 1H), 5.18 (s, 2H), 2.16 (s, 3H)

EXAMPLE 43

Preparation of acetic acid 6-[4-(6-bromo-1H-imidazo[4,5-b]pyridin-2-yl)-phenyl]-5-chloro-pyridin-3-yl methyl ester (56)

0.19 g of acetic acid 6-[4-(6-bromo-1H-imidazo[4,5-b]pyridin-2-yl)-phenyl]-5-chloro-pyridin-3-yl methyl ester (yield 85%) was obtained in the same manner as Example 40, except that compound (31) prepared in Example 19 was used instead of compound (28) in Example 40.

¹H NMR (CDCl₃) δ: 8.62 (s, 1H), 8.51 (s, 1H), 8.24 (s, 1H), 7.90-7.80 (m, 3H), 7.79 (d, 2H), 5.17 (s, 2H), 2.16 (s, 3H)

EXAMPLE 44

Preparation of acetic acid 6-[4-(4-bromo-6-trifluoromethyl-1H-benzoimidazol-2-yl)-phenyl]-5-chloro-pyridin-3-yl methyl ester (57)

0.24 g of acetic acid 6-[4-(4-bromo-6-trifluoromethyl-1H-benzoimidazol-2-yl)-phenyl]-5-chloro-pyridin-3-yl methyl ester (yield 93%) was obtained in the same manner as Example 40, except that compound (32) prepared in Example 20 was used instead of compound (28) in Example 40.

¹H NMR (CDCl₃) δ: 8.63 (s, 1H), 8.08 (d, 2H), 7.87 (dd, 1H), 7.74 (d, 2H), 7.68 (s, 1H), 5.16 (s, 2H), 2.16 (s, 3H)

EXAMPLE 45

Preparation of 5-chloro-6-[4-(6-trifluoromethyl-1H-benzoimidazol-2-yl)-phenyl]-pyridine-3-carbaldehyde (58)

4.4 g of manganese dioxide (51 mmol) was added to 1.0 g of compound (28) (2.6 mmol) prepared in Example 16 dissolved in 6.5 mL of dichloromethane, and stirred at room temperature for 2 hours. The mixture was filtered with diatomaceous earth, and the filtrate was concentrated under reduced pressure. The residue was separated by column chromatography (eluting solvent: chloroform/methanol=30/1) to obtain 0.94 g of 5-chloro-6-[4-(6-trifluoromethyl-1H-benzoimidazol-2-yl)-phenyl]-pyridine-3-carbaldehyde (yield 90%).

¹H NMR (CDCl₃) δ: 10.14 (s, 1H), 9.03 (s, 1H), 8.28 (s, 1H), 8.17 (d, 2H), 7.92 (d, 2H), 7.81 (s, 1H), 7.53 (brs, 1H), 7.50 (brs, 1H)

EXAMPLE 46

Preparation of 6-[4-(6-tert-butyl-1H-benzoimidazol-2-yl)-phenyl]-5-chloro-pyridine-3-carbaldehyde (59)

0.88 g of 6-[4-(6-tert-butyl-1H-benzoimidazol-2-yl)-phenyl]-5-chloro-pyridine-3-carbaldehyde (yield 87%) was obtained in the same manner as Example 45, except that compound (29) prepared in Example 17 was used instead of compound (28) in Example 45.

¹H NMR (CDCl₃) δ: 10.14 (s, 1H), 9.04 (s, 1H), 8.27 (d, 2H), 8.20 (d, 2H), 7.93 (d, 1H), 7.69 (s, 1H), 7.61 (d, 1H), 7.38 (d, 1H), 1.38 (s, 9H)

EXAMPLE 47

Preparation of 6-[4-(6-bromo-1H-benzoimidazol-2-yl)-phenyl]-5-chloro-pyridine-3-carbaldehyde (60)

0.91 g of 6-[4-(6-bromo-1H-benzoimidazol-2-yl)-phenyl]-5-chloro-pyridine-3-carbaldehyde (yield 85%) was obtained in the same manner as Example 45, except that compound (30) prepared in Example 18 was used instead of compound (28) in Example 45.

¹H NMR (CDCl₃) δ: 10.14 (s, 1H), 9.03 (s, 1H), 8.25 (s, 1H), 8.14 (d, 2H), 7.87 (d, 2H), 7.77 (s, 1H), 7.49 (brs, 1H), 7.42 (brs, 1H)

EXAMPLE 48

Preparation of 5-chloro-N-ethyl-6-[4-(6-trifluoromethyl-1H-benzoimidazol-2-yl)-phenyl]-nicotinamide (61)

0.10 g of 5-chloro-N-ethyl-6-(4-formyl-phenyl)-nicotinamide(6) (0.46 mmol) prepared in Example 3 and 0.08 g of 4-trifluoromethyl-benzene-1,2-diamine(20) (0.46 mmol) were dissolved in nitrobenzene (1.2 mL), and refluxed under heating for 2 hours. The reactant was cooled to room temperature, and concentrated under reduced pressure. The residue was separated by column chromatography (eluting solvent: chloroform/methanol=10/1) to obtain 0.18 g of 5-chloro-N-ethyl-6-[4-(6-trifluoromethyl-1H-benzoimidazol-2-yl)-phenyl]-nicotinamide (yield 89%).

¹H NMR (CD₃OD) δ: 9.02 (d, 1H), 8.41 (d, 1H), 8.27 (d, 2H), 8.01 (d, 2H), 8.00 (s, 1H), 7.86 (d, 1H), 7.68 (d, 1H), 3.46 (m, 2H), 1.26 (t, 3H)

EXAMPLE 49

Preparation of 6-[4-(6-tert-butyl-1H-benzoimidazol-2-yl)-phenyl]-5-chloro-N-ethyl-nicotinamide (62)

0.18 g of 6-[4-(6-tert-butyl-1H-benzoimidazol-2-yl)-phenyl]-5-chloro-N-ethyl-nicotinamide (yield 90%) was obtained in the same manner as Example 48, except that compound (21) was used instead of compound (20) in Example 48.

¹H NMR (CD₃OD) δ: 9.00 (d, 1H), 8.39 (d, 1H), 8.21 (d, 2H), 7.94 (d, 2H), 7.66 (d, 1H), 7.59 (d, 1H), 7.45 (dd, 1H), 3.46 (m, 2H), 1.41 (s, 9H), 1.26 (t, 3H)

EXAMPLE 50

Preparation of 6-[4-(6-bromo-1H-benzoimidazol-2-yl)-phenyl]-5-chloro-N-ethyl-nicotinamide (63)

0.18 g of 6-[4-(6-bromo-1H-benzoimidazol-2-yl)-phenyl]-5-chloro-N-ethyl-nicotinamide (yield 85%) was obtained in the same manner as Example 48, except that compound (22) was used instead of compound (20) in Example 48.

¹H NMR (CD₃OD) δ: 8.96 (s, 1H), 8.42 (s, 1H), 8.25 (d, 2H), 7.99 (d, 2H), 7.56 (d, 1H), 7.49 (d, 1H), 3.46 (q, 2H), 1.26 (t, 3H)

EXAMPLE 51

Preparation of 6-[4-(6-bromo-1H-imidazo[4,5-b]pyridin-2-yl)-phenyl]-5-chloro-N-ethyl-nicotinamide (64)

0.16 g of 6-[4-(6-bromo-1H-imidazo[4,5-b]pyridin-2-yl)-phenyl]-5-chloro-N-ethyl-nicotinamide (yield 75%) was obtained in the same manner as Example 48, except that compound (23) was used instead of compound (20) in Example 48.

¹H NMR (CD₃OD) δ: 8.95 (s, 1H), 8.43 (s, 1H), 8.27 (d, 2H), 8.11 (d, 1H), 7.90-7.84 (m, 3H), 3.46 (q, 2H), 1.26 (t, 3H)

EXAMPLE 52

Preparation of 6-[4-(4-bromo-6-trifluoromethyl-1H-benzoimidazol-2-yl)-phenyl]-5-chloro-N-ethyl-nicotinamide (65)

0.21 g of 6-[4-(4-bromo-6-trifluoromethyl-1H-benzoimidazol-2-yl)-phenyl]-5-chloro-N-ethyl-nicotinamide (yield 88%) was obtained in the same manner as Example 48, except that compound (24) was used instead of compound (20) in Example 48.

$^1$H NMR (CD$_3$OD) δ: 9.03 (d, 1H), 8.43 (d, 1H), 8.35 (d, 2H), 8.03 (d, 2H), 7.99 (s, 1H), 7.87 (s, 1H), 3.47 (m, 2H), 1.27 (t, 3H)

EXAMPLE 53

Preparation of 3-chloro-6'-(6-trifluoromethyl-1H-benzoimidazol-2-yl)-5-vinyl-[2,3']bipyridinyl (66)

0.1 g of compound (15) (0.4 mmol) prepared in Example 11 and 0.07 g of 4-chlorobenzene-1,2-diamine(20) (0.4 mmol) were dissolved in nitrobenzene (1 mL), and refluxed under heating for 2 hours. The reactant was cooled to room temperature, and concentrated under reduced pressure. The residue was separated by column chromatography (eluting solvent: chloroform/methanol=10/1) to obtain 0.12 g of 3-chloro-6'-(6-trifluoromethyl-1H-benzoimidazol-2-yl)-5-vinyl-[2,3']bipyridinyl (yield 77%).

$^1$H NMR (CDCl$_3$) δ: 9.09 (s, 1H), 8.64 (s, 1H), 8.55 (d, 1H), 8.34 (d, 1H), 8.00 (brs, 1H), 7.88 (s, 1H), 7.72 (brs, 1H), 7.54 (d, 1H), 6.78-6.68 (m, 1H), 5.95 (d, 1H), 5.53 (d, 1H)

EXAMPLE 54

Preparation of 6'-(6-tert-butyl-1H-benzoimidazol-2-yl)-3-chloro-5-vinyl-[2,3']bipyridinyl (67)

0.11 g of 6'-(6-tert-butyl-1H-benzoimidazol-2-yl)-3-chloro-5-vinyl-[2,3']bipyridinyl (yield 70%) was obtained in the same manner as Example 53, except that compound (21) was used instead of compound (20) in Example 53.

$^1$H NMR (CDCl$_3$) δ: 9.06 (s, 1H), 8.63 (s, 1H), 8.54 (d, 1H), 8.29 (d, 1H), 7.87 (s, 1H), 7.55-7.51 (brs, 2H), 7.40 (d, 1H), 6.77-6.68 (m, 1H), 5.93 (d, 1H), 1.40 (s, 9H)

EXAMPLE 55

Preparation of 6'-(6-bromo-1H-benzoimidazol-2-yl)-3-chloro-5-vinyl-[2,3']bipyridinyl (68)

0.14 g of 6'-(6-bromo-1H-benzoimidazol-2-yl)-3-chloro-5-vinyl-[2,3']bipyridinyl (yield 86%) was obtained in the same manner as Example 53, except that compound (22) was used instead of compound (20) in Example 53.

$^1$H NMR (CDCl$_3$) δ: 9.06 (s, 1H), 8.63 (s, 1H), 8.48 (t, 2H), 8.32-8.25 (m, 3H), 7.88 (s, 1H), 6.74-6.65 (m, 1H), 5.94 (d, 1H), 5.53 (d, 1H)

EXAMPLE 56

Preparation of 3-chloro-6'-(6-chloro-1H-benzoimidazol-2-yl)-5-vinyl-[2,3']bipyridinyl (69)

0.12 g of 3-chloro-6'-(6-chloro-1H-benzoimidazol-2-yl)-5-vinyl-[2,3']bipyridinyl (yield 82%) was obtained in the same manner as Example 53, except that compound (23) was used instead of compound (20) in Example 53.

$^1$H NMR (CDCl$_3$) δ: 10.76 (brs, 1H), 9.06 (s, 1H), 8.64 (s, 1H), 8.49 (d, 1H), 8.31 (d, 1H), 7.88 (s, 1H), 7.76 (brs, 1H), 7.61 (brs, 1H), 7.35 (s, 1H), 6.78-6.68 (m, 1H), 5.95 (d, 1H), 5.53 (d, 1H)

EXAMPLE 57

Preparation of 6'-(4-bromo-6-trifluoromethyl-1H-benzoimidazol-2-yl)-3-chloro-5-vinyl-[2,3']bipyridinyl (70)

0.13 g of 6'-(4-bromo-6-trifluoromethyl-1H-benzoimidazol-2-yl)-3-chloro-5-vinyl-[2,3']bipyridinyl (yield 70%) was obtained in the same manner as Example 53, except that compound (24) was used instead of compound (20) in Example 53.

$^1$H NMR (CDCl$_3$) δ: 9.17 (s, 1H), 8.76 (s, 1H), 8.65 (s, 1H), 8.29 (s, 1H), 7.89-7.88 (m, 1H), 7.67 (d, 1H), 7.31 (d, 1H), 6.78-6.69 (m, 1H), 5.95 (d, 1H), 5.54 (d, 1H)

EXAMPLE 58

Preparation of 3-chloro-6'-(6-morpholin-4-yl-1H-benzoimidazol-2-yl)-[2,3']bipyridinyl-5-carboxylic acid methyl ester (71)

0.50 g of 3-chloro-6'-formyl-[2,3']bipyridyl-5-carboxylic acid methyl ester (13) (1.81 mmol) prepared in Example 9 and 0.35 g of 4-morpholinobenzene-1,2-diamine(18) (1.81 mmol) prepared in Example 12 were dissolved in nitrobenzene (5.0 mL), and refluxed under heating for 2 hours. The reactant was cooled to room temperature, and concentrated under reduced pressure. The residue was separated by column chromatography (eluting solvent: ethyl acetate/hexane=1/1) to obtain 0.55 g of 3-chloro-6'-(6-morpholin-4-yl-1H-benzoimidazol-2-yl)-[2,3']bipyridinyl-5-carboxylic acid methyl ester (yield 68%).

$^1$H NMR (CD$_3$OD) δ: 9.16 (s, 1H), 9.10 (s, 1H), 8.52 (s, 1H), 8.35 (s, 2H), 7.58 (br, 1H), 7.12 (br, 2H), 4.00 (s, 3H), 3.88 (m, 4H), 3.41 (m, 4H)

EXAMPLE 59

Preparation of 3-chloro-6'-[6-(4-methyl-piperazin-1-yl)-1H-benzoimidazol-2-yl]-[2,3']bipyridinyl-5-carboxylic acid methyl ester (72)

0.54 g of 3-chloro-6'-[6-(4-methyl-piperazin-1-yl)-1H-benzoimidazol-2-yl]-[2,3']bipyridinyl-5-carboxylic acid methyl ester (yield 66%) was obtained in the same manner as Example 58, except that compound (19) prepared in Example 13 was used instead of compound (18) in Example 58.

$^1$H NMR (CDCl$_3$) δ: 9.14 (s, 1H), 9.08 (s, 1H), 8.50 (s, 1H), 8.34 (m, 2H), 7.56 (d, 1H), 7.12 (br, 2H), 3.99 (s, 3H), 3.26 (m, 4H), 2.72 (m, 4H), 2.41 (s, 3H)

EXAMPLE 60

Preparation of 3-chloro-6'-(6-trifluoromethyl-1H-benzoimidazol-2-yl)-[2,3']bipyridinyl-5-carboxylic acid methyl ester (73)

0.67 g of 3-chloro-6'-(6-trifluoromethyl-1H-benzoimidazol-2-yl)-[2,3']bipyridinyl-5-carboxylic acid methyl ester (yield 86%) was obtained in the same manner as Example 58, except that compound (20) was used instead of compound (18) in Example 58.

$^1$H NMR (CDCl$_3$) δ: 9.19 (s, 1H), 9.09 (s, 1H), 8.77 (d, 1H), 8.44 (s, 1H), 8.40 (d, 1H), 8.07 (s, 1H), 7.85 (d, 1H), 7.61 (d, 1H), 4.02 (s, 3H)

EXAMPLE 61

Preparation of 6'-(6-tert-butyl-1H-benzoimidazol-2-yl)-3-chloro-[2,3']bipyridinyl-5-carboxylic acid methyl ester (74)

0.62 g of 6'-(6-tert-butyl-1H-benzoimidazol-2-yl)-3-chloro-[2,3']bipyridinyl-5-carboxylic acid methyl ester (yield 81%) was obtained in the same manner as Example 58, except that compound (21) was used instead of compound (18) in Example 58.

$^1$H NMR (CDCl$_3$) δ: 9.18 (s, 1H), 9.06 (s, 1H), 8.61 (d, 1H), 8.41 (s, 1H), 8.31 (d, 1H), 7.67 (s, 1H), 7.62 (d, 1H), 7.39 (d, 1H), 3.99 (s, 3H), 1.37 (s, 9H)

EXAMPLE 62

Preparation of 6'-(6-bromo-1H-benzoimidazol-2-yl)-3-chloro-[2,3']bipyridinyl-5-carboxylic acid methyl ester (75)

0.64 g of 6'-(6-bromo-1H-benzoimidazol-2-yl)-3-chloro-[2,3']bipyridinyl-5-carboxylic acid methyl ester (yield 80%) was obtained in the same manner as Example 58, except that compound (22) was used instead of compound (18) in Example 58.

$^1$H NMR (CDCl$_3$) δ: 9.18 (m, 2H), 8.53 (s, 1H), 8.46 (d, 1H), 8.40 (d, 1H), 7.92 (s, 1H), 7.67 (d, 1H), 7.57 (d, 1H), 4.00 (s, 3H)

EXAMPLE 63

Preparation of 6'-(6-bromo-1H-imidazo[4,5-b]pyridin-2-yl)-3-chloro-[2,3']bipyridinyl-5-carboxylic acid methyl ester (76)

0.56 g of 6'-(6-bromo-1H-imidazo[4,5-b]pyridin-2-yl)-3-chloro-[2,3']bipyridinyl-5-carboxylic acid methyl ester (yield 70%) was obtained in the same manner as Example 58, except that compound (23) was used instead of compound (18) in Example 58.

$^1$H NMR (CDCl$_3$) δ: 9.21 (s, 1H), 9.15 (s, 1H), 8.68 (m, 2H), 8.42 (s, 1H), 8.35 (d, 1H), 7.95 (s, 1H), 4.01 (s, 3H)

EXAMPLE 64

Preparation of 6'-(4-bromo-6-trifluoromethyl-1H-benzoimidazol-2-yl)-3-chloro-[2,3']bipyridinyl-5-carboxylic acid methyl ester (77)

0.72 g of 6'-(4-bromo-6-trifluoromethyl-1H-benzoimidazol-2-yl)-3-chloro-[2,3']bipyridinyl-5-carboxylic acid methyl ester (yield 78%) was obtained in the same manner as Example 58, except that compound (24) was used instead of compound (18) in Example 58.

$^1$H NMR (CDCl$_3$) δ: 9.11 (s, 1H), 9.02 (s, 1H), 8.53 (d, 1H), 8.38 (s, 1H), 8.29 (d, 1H), 7.84 (s, 1H), 7.64 (s, 1H), 3.93 (s, 3H)

EXAMPLE 65

Preparation of 3-chloro-6'-(4,6-dibromo-1H-benzoimidazol-2-yl)-[2,3']bipyridinyl-5-carboxylic acid methyl ester (78)

0.68 g of 3-chloro-6'-(4,6-dibromo-1H-benzoimidazol-2-yl)-[2,3']bipyridinyl-5-carboxylic acid methyl ester (yield 72%) was obtained in the same manner as Example 58, except that compound (25) was used instead of compound (18) in Example 58.

$^1$H NMR (CDCl$_3$) δ: 9.25 (s, 1H), 9.22 (s, 1H), 8.80 (d, 1H), 8.72 (d, 1H), 8.49 (s, 1H), 7.87 (br, 2H), 4.03 (s, 3H)

EXAMPLE 66

Preparation of 3-chloro-6'-(6-morpholin-4-yl-1H-benzoimidazol-2-yl)-[2,3']bipyridinyl-5-carboxylic acid (79)

4 mL of 2 M lithium hydroxide solution (methanol/water=3/1) was added to 0.55 g of 3-chloro-6'-(6-morpholin-4-yl-1H-benzoimidazol-2-yl)-[2,3']bipyridinyl-5-carboxylic acid methyl ester (71) (1.22 mmol) prepared in Example 58, and stirred at room temperature for 6 hours. The mixture was concentrated under reduced pressure, dissolved in ethyl acetate, and washed with water. The organic layer was dried over magnesium sulfate, and concentrated under reduced pressure. The residue was separated by column chromatography (eluting solvent: chloroform/methanol=5/1) to obtain 0.49 g of yellow crystal, 3-chloro-6'-(6-morpholin-4-yl-1H-benzoimidazol-2-yl)-[2,3']bipyridinyl-5-carboxylic acid (yield 92%).

$^1$H NMR (DMSO-d$_6$) δ: 9.20 (s, 1H), 9.16 (s, 1H), 8.70 (d, 1H), 8.59 (d, 1H), 8.50 (s, 1H), 7.71 (d, 2H), 7.44 (d, 1H), 7.20 (s, 1H)

EXAMPLE 67

Preparation of 3-chloro-6'-[6-(4-methyl-piperazin-1-yl)-1H-benzoimidazol-2-yl]-[2,3']bipyridinyl-5-carboxylic acid (80)

0.49 g of 3-chloro-6'-[6-(4-methyl-piperazin-1-yl)-1H-benzoimidazol-2-yl]-[2,3']bipyridinyl-5-carboxylic acid (yield 89%) was obtained in the same manner as Example 66, except that compound (72) prepared in Example 59 was used instead of compound (71) in Example 66.

$^1$H NMR (DMSO-d$_6$) δ: 9.20 (s, 1H), 9.16 (s, 1H), 8.75 (d, 1H), 8.56 (dd, 1H), 8.50 (s, 1H), 7.73 (d, 1H), 7.39 (d, 2H), 7.18 (s, 1H), 2.84 (s, 3H)

EXAMPLE 68

Preparation of 3-chloro-6'-(6-trifluoromethyl-1H-benzoimidazol-2-yl)-[2,3']bipyridinyl-5-carboxylic acid (81)

0.49 g of 3-chloro-6'-(6-trifluoromethyl-1H-benzoimidazol-2-yl)-[2,3']bipyridinyl-5-carboxylic acid (yield 96%) was obtained in the same manner as Example 66, except that compound (73) prepared in Example 60 was used instead of compound (71) in Example 66.

$^1$H NMR (DMSO-d$_6$) δ: 9.15 (s, 2H), 8.54-8.43 (m, 3H), 8.02 (s, 1H), 7.85 (d, 1H), 7.60 (d, 1H)

EXAMPLE 69

Preparation of 6'-(6-tert-butyl-1H-benzoimidazol-2-yl)-3-chloro-[2,3']bipyridinyl-5-carboxylic acid (82)

0.46 g of 6'-(6-tert-butyl-1H-benzoimidazol-2-yl)-3-chloro-[2,3']bipyridinyl-5-carboxylic acid (yield 93%) was obtained in the same manner as Example 66, except that compound (74) prepared in Example 61 was used instead of compound (71) in Example 66.

$^1$H NMR (DMSO-$d_6$) δ: 9.14 (s, 2H), 8.56-8.47 (m, 3H), 7.68-7.65 (m, 2H), 7.51 (d, 1H), 1.30 (s, 9H)

EXAMPLE 70

Preparation of 6'-(6-bromo-1H-benzoimidazol-2-yl)-3-chloro-[2,3']bipyridinyl-5-carboxylic acid (83)

0.47 g of 6'-(6-bromo-1H-benzoimidazol-2-yl)-3-chloro-[2,3']bipyridinyl-5-carboxylic acid (yield 90%) was obtained in the same manner as Example 66, except that compound (75) prepared in Example 62 was used instead of compound (71) in Example 66.

$^1$H NMR (DMSO-$d_6$) δ: 9.13 (s, 1H), 9.10 (s, 1H), 8.49-8.35 (m, 3H), 7.82 (s, 1H), 7.61 (d, 1H), 7.39 (d, 1H)

EXAMPLE 71

Preparation of 6'-(6-bromo-1H-imidazo[4,5-b]pyridin-2-yl)-3-chloro-[2,3']bipyridinyl-5-carboxylic acid (84)

0.42 g of 6'-(6-bromo-1H-imidazo[4,5-b]pyridin-2-yl)-3-chloro-[2,3']bipyridinyl-5-carboxylic acid (yield 80%) was obtained in the same manner as Example 66, except that compound (76) prepared in Example 63 was used instead of compound (71) in Example 66.

$^1$H NMR (DMSO-$d_6$) δ: 9.10 (s, 1H), 9.03 (s, 1H), 8.51-8.44 (m, 3H), 8.07 (d, 1H), 7.42 (s, 1H)

EXAMPLE 72

Preparation of 6'-(4-bromo-6-trifluoromethyl-1H-benzoimidazol-2-yl)-3-chloro-[2,3']bipyridinyl-5-carboxylic acid (85)

0.53 g of 6'-(4-bromo-6-trifluoromethyl-1H-benzoimidazol-2-yl)-3-chloro-[2,3']bipyridinyl-5-carboxylic acid (yield 87%) was obtained in the same manner as Example 66, except that compound (77) prepared in Example 64 was used instead of compound (71) in Example 66.

$^1$H NMR (DMSO-$d_6$) δ: 9.16 (s, 2H), 8.55 (d, 1H), 8.48-8.43 (m, 2H), 7.88 (s, 1H), 7.81 (s, 1H)

EXAMPLE 73

Preparation of 3-chloro-6'-(4,6-dibromo-1H-benzoimidazol-2-yl)-[2,3']bipyridinyl-5-carboxylic acid (86)

0.53 g of 3-chloro-6'-(4,6-dibromo-1H-benzoimidazol-2-yl)-[2,3']bipyridinyl-5-carboxylic acid (yield 85%) was obtained in the same manner as Example 66, except that compound (78) prepared in Example 65 was used instead of compound (71) in Example 66.

$^1$H NMR (DMSO-$d_6$) δ: 9.15 (s, 2H), 8.53-8.41 (m, 3H), 7.73 (s, 1H), 7.68 (s, 1H)

EXAMPLE 74

Preparation of [3-chloro-6'-(6-morpholin-4-yl-1H-benzoimidazol-2-yl)-[2,3']bipyridinyl-5-yl]-methanol compound (87)

0.49 g of 3-chloro-6'-(6-morpholin-4-yl-1H-benzoimidazol-2-yl)-[2,3']bipyridinyl-5-carboxylic acid (71) (1.12 mmol) prepared in Example 58 was added to 5 mL of tetrahydrofuran, and cooled to −80° C. 0.09 g of lithium aluminum hydroxide (2.24 mmol) was slowly added thereto. After stirring for 2 hours, the temperature of the reactant was slowly raised to room temperature, and further reacted 2 hours. A small amount of water was added thereto terminate the reaction, and concentrated under reduced pressure. Then, the resultant was dissolved in ethyl acetate and washed with water. The organic layer was dried over magnesium sulfate, and concentrated under reduced pressure. The residue was separated by column chromatography (eluting solvent: chloroform/methanol=20/1) to obtain 0.44 g of yellow crystal, [3-chloro-6'-(6-morpholin-4-yl-1H-benzoimidazol-2-yl)-[2,3']bipyridinyl-5-yl]-methanol compound (yield 93%).

$^1$H NMR (CD$_3$OD) δ: 9.02 (s, 1H), 8.61 (s, 1H), 8.35-8.29 (m, 2H), 8.02 (s, 1H), 7.59 (d, 1H), 7.15-7.10 (m, 2H), 4.74 (s, 2H), 3.90-3.87 (m, 4H), 3.21-3.18 (m, 4H)

EXAMPLE 75

Preparation of {3-chloro-6'-[6-(4-methyl-piperazin-1-yl)-1H-benzoimidazol-2-yl]-[2,3']bipyridinyl-5-yl}-methanol (88)

0.41 g of {3-chloro-6'-[6-(4-methyl-piperazin-1-yl)-1H-benzoimidazol-2-yl]-[2,3']bipyridinyl-5-yl}-methanol (yield 84%) was obtained in the same manner as Example 74, except that compound (72) prepared in Example 59 was used instead of compound (71) in Example 74.

$^1$H NMR (DMSO-$d_6$) δ: 9.00 (s, 1H), 8.59 (s, 1H), 8.33-8.25 (m, 2H), 8.00 (s, 1H), 7.62 (d, 1H), 7.20-7.12 (m, 2H), 4.74 (s, 2H), 3.26 (m, 4H), 2.72 (m, 4H), 2.41 (s, 3H)

EXAMPLE 76

Preparation of [3-chloro-6'-(6-trifluoromethyl-1H-benzoimidazol-2-yl)-[2,3']bipyridinyl-5-yl]-methanol (89)

0.41 g of [3-chloro-6'-(6-trifluoromethyl-1H-benzoimidazol-2-yl)-[2,3']bipyridinyl-5-yl]-methanol (yield 90%) was obtained in the same manner as Example 74, except that compound (73) prepared in Example 60 was used instead of compound (71) in Example 74.

$^1$H NMR (DMSO-$d_6$) δ: 9.14 (s, 1H), 8.54 (s, 1H), 8.39 (s, 2H), 8.06 (s, 1H), 7.91-7.89 (m, 2H), 7.76 (d, 1H)

EXAMPLE 77

Preparation of [6'-(6-tert-butyl-1H-benzoimidazol-2-yl)-3-chloro-[2,3']bipyridinyl-5-yl]-methanol (90)

0.42 g of [6'-(6-tert-butyl-1H-benzoimidazol-2-yl)-3-chloro-[2,3']bipyridinyl-5-yl]-methanol (yield 95%) was obtained in the same manner as Example 74, except that compound (74) prepared in Example 61 was used instead of compound (71) in Example 74.

$^1$H NMR (CDCl$_3$) δ: 8.93 (s, 1H), 8.53 (s, 1H), 8.42 (d, 1H), 8.21 (dd, 1H), 7.87 (s, 1H), 7.63-7.58 (m, 2H), 7.36 (dd, 1H)

EXAMPLE 78

Preparation of [6'-(6-bromo-1H-benzoimidazol-2-yl)-3-chloro-[2,3']bipyridinyl-5-yl]-methanol (91)

0.41 g of [6'-(6-bromo-1H-benzoimidazol-2-yl)-3-chloro-[2,3']bipyridinyl-5-yl]-methanol (yield 88%) was obtained in the same manner as Example 74, except that compound (75) prepared in Example 62 was used instead of compound (71) in Example 74.

$^1$H NMR (CD$_3$OD) δ: 9.13 (s, 1H), 8.52 (s, 1H), 8.35 (d, 2H), 7.91 (d, 2H), 7.64 (s, 2H)

EXAMPLE 79

Preparation of [6'-(6-bromo-1H-imidazo[4,5-b]pyridin-2-yl)-3-chloro-[2,3']bipyridinyl-5-yl]-methanol (92)

0.35 g of [6'-(6-bromo-1H-imidazo[4,5-b]pyridin-2-yl)-3-chloro-[2,3']bipyridinyl-5-yl]-methanol (yield 75%) was obtained in the same manner as Example 74, except that compound (76) prepared in Example 63 was used instead of compound (71) in Example 74.

$^1$H NMR (CD$_3$OD) δ: 9.11 (s, 1H), 8.64 (s, 1H), 8.50 (d, 1H), 8.38 (d, 1H), 8.14 (d, 1H), 7.44 (d, 1H), 4.75 (s, 2H)

EXAMPLE 80

Preparation of [6'-(4-bromo-6-trifluoromethyl-1H-benzoimidazol-2-yl)-3-chloro-[2,3']bipyridinyl-5-yl]-methanol (93)

0.46 g of [6'-(4-bromo-6-trifluoromethyl-1H-benzoimidazol-2-yl)-3-chloro-[2,3']bipyridinyl-5-yl]-methanol (yield 85%) was obtained in the same manner as Example 74, except that compound (77) prepared in Example 64 was used instead of compound (71) in Example 74.

$^1$H NMR (CD$_3$OD) δ: 9.07 (d, 1H), 8.62 (s, 1H), 8.59 (d, 1H), 8.33 (d, 1H), 7.97 (s, 1H), 7.93 (s, 1H), 7.72 (s, 1H), 4.83 (s, 2H)

EXAMPLE 81

Preparation of [3-chloro-6'-(4,6-dibromo-1H-benzoimidazol-2-yl)-[2,3']bipyridinyl-5-yl]-methano l (94)

0.44 g of [3-chloro-6'-(4,6-dibromo-1H-benzoimidazol-2-yl)-[2,3']bipyridinyl-5-yl]-methanol (yield 79%) was obtained in the same manner as Example 74, except that compound (78) prepared in Example 65 was used instead of compound (71) in Example 74.

$^1$H NMR (CD$_3$OD) δ: 8.85 (s, 1H), 8.63-8.55 (m, 3H), 8.17 (d, 1H), 8.01 (s, 1H), 7.57 (d, 1H), 4.72 (s, 2H)

EXAMPLE 82

Preparation of 3-chloro-6'-(6-morpholin-4-yl-1H-benzoimidazol-2-yl)-[2,3']bipyridinyl-5-carboxylic acid ethyl amide (95)

0.43 g of O-(7-azabenzotriazol-1-yl)-N,N,N',N'-tetramethyluronium hexafluorophosphine (1.12 mmol) was added to 0.49 g of 3-chloro-6'-(6-morpholin-4-yl-1H-benzoimidazol-2-yl)-[2,3']bipyridinyl-5-carboxylic acid (79) (1.12 mmol) prepared in Example 66 dissolved in 1.0 mL of tetrahydrofuran and 1.0 mL of dimethylformamide, and stirred at room temperature for 10 minutes. 0.56 mL of ethylamine (1.12 mmol) in 2.0 M tetrahydrofuran solution was added thereto, and refluxed under heating and stirring for 18 hours. The mixture was cooled to room temperature, and concentrated under reduced pressure. Then, the mixture was dissolved in ethyl acetate, and washed with water. The organic layer was dried over magnesium sulfate, and concentrated under reduced pressure. The residue was separated by column chromatography (eluting solvent: chloroform/methanol=20/1) to obtain 0.35 g of 3-chloro-6'-(6-morpholin-4-yl-1H-benzoimidazol-2-yl)-[2,3']bipyridinyl-5-carboxylic acid ethyl amide (yield 68%).

$^1$H NMR (CD$_3$OD) δ: 9.18 (s, 1H), 9.04 (s, 1H), 8.41 (s, 1H), 7.97 (s, 2H), 7.62 (d, 1H), 7.20 (m, 2H), 3.88-3.87 (m, 4H), 3.47 (q, 2H), 3.23-3.15 (m, 4H), 1.27 (t, 3H)

EXAMPLE 83

Preparation of 3-chloro-6'-[6-(4-methyl-piperazin-1-yl)-1H-benzoimidazol-2-yl]-[2,3']bipyridinyl-5-carboxylic acid ethyl amide (96)

0.37 g of 3-chloro-6'-[6-(4-methyl-piperazin-1-yl)-1H-benzoimidazol-2-yl]-[2,3']bipyridinyl-5-carboxylic acid ethyl amide (yield 69%) was obtained in the same manner as Example 82, except that compound (80) prepared in Example 67 was used instead of compound (79) in Example 82.

$^1$H NMR (CD$_3$OD) δ: 9.11 (s, 1H), 9.02 (s, 1H), 8.44 (s, 1H), 7.97 (m, 2H), 7.62 (d, 1H), 7.22 (m, 2H), 3.47 (q, 2H), 3.26 (m, 4H), 2.72 (m, 4H), 2.41 (s, 3H), 1.27 (t, 3H)

EXAMPLE 84

Preparation of 3-chloro-6'-(6-trifluoromethyl-1H-benzoimidazol-2-yl)-[2,3']bipyridinyl-5-carboxylic acid ethyl amide (97)

0.45 g of 3-chloro-6'-(6-trifluoromethyl-1H-benzoimidazol-2-yl)-[2,3']bipyridinyl-5-carboxylic acid ethyl amide (yield 90%) was obtained in the same manner as Example 82, except that compound (81) prepared in Example 68 was used instead of compound (79) in Example 82.

$^1$H NMR (CD$_3$OD) δ: 9.14 (s, 1H), 9.05 (s, 1H), 8.43-7.36 (m, 3H), 8.01 (s, 1H), 7.84 (d, 1H), 7.60 (d, 1H), 3.44 (q, 2H), 1.27 (t, 3H)

EXAMPLE 85

Preparation of 6'-(6-tert-butyl-1H-benzoimidazol-2-yl)-3-chloro-[2,3']bipyridinyl-5-carboxylic acid ethyl amide (98)

0.46 g of 6'-(6-tert-butyl-1H-benzoimidazol-2-yl)-3-chloro-[2,3']bipyridinyl-5-carboxylic acid ethyl amide (yield 95%) was obtained in the same manner as Example 82, except that compound (82) prepared in Example 69 was used instead of compound (79) in Example 82.

$^1$H NMR (CD$_3$OD) δ: 9.12 (s, 1H), 9.04 (s, 1H), 8.42-8.38 (m, 2H), 7.97 (s, 1H), 7.75 (s, 1H), 7.61 (d, 1H), 7.45 (d, 1H), 3.45 (q, 2H), 1.42 (s, 9H), 1.26 (t, 3H)

EXAMPLE 86

Preparation of 6'-(6-bromo-1H-benzoimidazol-2-yl)-3-chloro-[2,3']bipyridinyl-5-carboxylic acid ethyl amide (99)

0.43 g of 6'-(6-bromo-1H-benzoimidazol-2-yl)-3-chloro-[2,3']bipyridinyl-5-carboxylic acid ethyl amide (yield 84%) was obtained in the same manner as Example 82, except that compound (83) prepared in Example 70 was used instead of compound (79) in Example 82.

$^1$H NMR (CD$_3$OD) δ: 9.12 (s, 1H), 9.03 (s, 1H), 8.56 (s, 1H), 8.41 (s, 1H), 8.24 (d, 1H), 7.85 (s, 1H), 7.73 (d, 1H), 7.42 (d, 1H), 3.47 (q, 2H), 1.26 (t, 3H)

EXAMPLE 87

Preparation of 6'-(6-bromo-1H-imidazo[4,5-b]pyridin-2-yl)-3-chloro-[2,3']bipyridinyl-5-carboxylic acid ethyl amide (100)

0.38 g of 6'-(6-bromo-1H-imidazo[4,5-b]pyridin-2-yl)-3-chloro-[2,3']bipyridinyl-5-carboxylic acid ethyl amide (yield 74%) was obtained in the same manner as Example 82, except that compound (84) prepared in Example 71 was used instead of compound (79) in Example 82.

$^1$H NMR (CD$_3$OD) δ: 9.18 (s, 1H), 9.06 (s, 1H), 8.56-8.48 (m, 2H), 8.40 (d, 1H), 8.31 (s, 1H), 8.12 (d, 1H), 3.44 (q, 2H), 1.27 (t, 3H)

EXAMPLE 88

Preparation of 6'-(4-bromo-6-trifluoromethyl-1H-benzoimidazol-2-yl)-3-chloro-[2,3']bipyridinyl-5-carboxylic acid ethyl amide (101)

0.47 g of 6'-(4-bromo-6-trifluoromethyl-1H-benzoimidazol-2-yl)-3-chloro-[2,3']bipyridinyl-5-carboxylic acid ethyl amide (yield 80%) was obtained in the same manner as Example 82, except that compound (85) prepared in Example 72 was used instead of compound (79) in Example 82.

$^1$H NMR (CD$_3$OD) δ: 9.15 (s, 1H), 9.05 (s, 1H), 8.61 (s, 2H), 8.42 (s, 1H), 8.30 (d, 1H), 7.97 (s, 1H), 7.76 (s, 1H), 3.45 (q, 2H), 1.27 (t, 3H)

EXAMPLE 89

Preparation of 3-chloro-6'-(4,6-dibromo-1H-benzoimidazol-2-yl)-[2,3']bipyridinyl-5-carboxylic acid ethyl amide (102)

0.43 g of 3-chloro-6'-(4,6-dibromo-1H-benzoimidazol-2-yl)-[2,3']bipyridinyl-5-carboxylic acid ethyl amide (yield 72%) was obtained in the same manner as Example 82, except that compound (86) prepared in Example 73 was used instead of compound (79) in Example 82.

$^1$H NMR (CD$_3$OD) δ: 9.10 (s, 1H), 9.05 (s, 1H), 8.68 (s, 1H), 8.66 (d, 1H), 8.36 (d, 1H), 7.82-7.76 (m, 2H), 3.44 (q, 2H), 1.27 (t, 3H)

EXPERIMENTAL EXAMPLE 1

Calcium Influx Test of Vanilloid Receptor

In order to measure an activity of the biaryl benzoimidazole derivative of the invention as an antagonist, a calcium influx test was performed.

1) Cell Culture

An hVR1-HEK293 cell line is a cell line, in which a Human Embryonic Kidney (HEK) 293 Tet-on cell is transformed with a human vanilloid-1 gene (pTRE2hyg-hVR1, 7.8 kb). The cell line can regulate a VR-1 expression, depending on the administration of a tetracycline analogue, doxycycline. At two days before the calcium influx test, the cell line was cultured in media containing doxycycline to induce the VR-1 expression, and then used. First, the hVR1-HEK293 cells were cultured in T75 flasks to have a density of about 80%, and then detached from the bottom of the flasks by using trypsin. The detached cells were centrifuged and collected. Then, the cells were suspended in media containing 1□/mL doxycycline, and diluted to have a concentration of $2×10^5$ to $4×10^5$ cells/mL. 100 μL of the suspended cells were added to each well of 96-well black plate, cultured at 37° C. and 5% $CO_2$ cell incubator for two days, and then used in the calcium influx test.

2) Preparation of Sample Compound

The compound was dissolved in dimethyl sulfoxide (DMSO), and then used for the calcium influx test.

3) Calcium Influx Measurement

In order to measure the calcium influx in vivo, the cells were cultured in a solution containing Fluo-3/AM, which is a calcium indicator, at 37° C. for 90 minutes, so as to be permeated by a fluorescent dye. Then, the cells were washed with D-PBS (Dulbecco's phosphate buffered saline) containing 10 mM HEPES three times, and the fluorescent dye that did not permeate into the cells was removed. 193 μL D-PBS were added to each well, and then the compound was added thereto in various concentrations. To measure an activity as an antagonist, the cells were treated with 1 μM capsaicin to stimulate the calcium influx. The inhibitory effect of the compound when calcium influx was induced by 1 μM capsaicin was measured depending on its concentration using a fluorescence spectrometer, and the obtained data were substituted into a hill equation to analyze the values.

The results of evaluating the inhibitory effect of the compounds of the invention on calcium influx are shown in Table 1. The inhibitory effect on calcium influx was measured with a single concentration of the compounds of the invention (200 nM), and the result thereof are shown in Table 2.

TABLE 1

Evaluation result of inhibitory effect of compounds of the invention on calcium influx

| Compound | Inhibitory effect IC$_{50}$ (nM) |
|---|---|
| 28 | 181.3 |
| 29 | 15.9 |
| 30 | 170.9 |
| 48 | 55.1 |
| 49 | 23.1 |
| 50 | 62.3 |
| 53 | 90.4 |
| 54 | 318.7 |
| 58 | 94.5 |
| 59 | 29.5 |
| 62 | 126.1 |
| 63 | 396.7 |
| 73 | 55.2 |
| 74 | 26.2 |
| 89 | 338.2 |
| 90 | 158.1 |
| 91 | 516.5 |
| 93 | 129.1 |

TABLE 2

Evaluation result of inhibitory effect on calcium influx with a single concentration of compounds of the invention (200 nM)

| Compound | Inhibitory effect (%) |
|---|---|
| 26 | 5 |
| 27 | 4 |
| 28 | 2.8 |
| 29 | 74.8 |
| 30 | 27.8 |
| 31 | 1.7 |
| 32 | 6 |
| 33 | 4.7 |
| 34 | 13 |
| 35 | 59.6 |
| 36 | 09.6 |
| 37 | 05.3 |
| 38 | 11.7 |
| 39 | 3.1 |
| 41 | −2.1 |
| 42 | 0.9 |
| 43 | −3.1 |
| 44 | −1 |
| 45 | 3.3 |
| 46 | 7.2 |
| 47 | 5.7 |
| 48 | 38.7 |
| 49 | 85 |
| 50 | 46.4 |
| 51 | 1.1 |
| 52 | 20 |
| 53 | 37.4 |
| 54 | 14.6 |
| 55 | 0.9 |
| 56 | 6.5 |
| 57 | 16.9 |
| 58 | 39.1 |
| 59 | 82.5 |
| 61 | 23.4 |
| 62 | 54.3 |
| 63 | 38.3 |
| 64 | 11.1 |
| 65 | 30.9 |
| 66 | 0.2 |
| 67 | −8.8 |
| 68 | −2.2 |
| 69 | 11.3 |
| 70 | 0 |
| 71 | 7.1 |
| 72 | −2.9 |
| 73 | 56.1 |
| 74 | 81.3 |
| 75 | 45.3 |
| 76 | 7 |
| 77 | 48.9 |
| 78 | 4.1 |
| 79 | 3.3 |
| 80 | −5 |
| 81 | 9.6 |
| 82 | 6.7 |
| 83 | 22.8 |
| 84 | 6.3 |
| 85 | 4.2 |
| 86 | −1.1 |
| 87 | 3.7 |
| 88 | 15.3 |
| 89 | 30 |
| 90 | 42.7 |
| 91 | 27.6 |
| 92 | 7.3 |
| 93 | 41 |
| 94 | 9.8 |
| 95 | −0.6 |
| 86 | 18.8 |
| 97 | 13.3 |
| 98 | 13.2 |
| 99 | 17.5 |
| 100 | 13 |
| 101 | 3.7 |
| 102 | 13.2 |

As shown in Tables 1 and 2, it was found that the biaryl benzoimidazole derivative of the invention has an excellent inhibitory effect on calcium influx in HEK cells, thereby showing a powerful antagonistic effect on the vanilloid receptor.

EXPERIMENTAL EXAMPLE 2

Analgesic Efficacy Test

In order to test analgesic efficacy of the biaryl benzoimidazole derivative of the invention, a PBQ-induced writhing test was performed using a mouse.

A 5-week-old ICR male mouse was used as an experimental animal, and PBQ (phenyl-p-quinone, 0.02%) was used as a chemical stimulator. 20 mg of the test material per mouse body weight were suspended in 10 mL solvent of Na-CMC and saline solution, and then used. At 1 hour before administering PBQ, the test material and excipient were orally administered, and 10 mL of PBQ per kg (body weight) were intraperitoneally administered. Between 5 to 10 minutes after administration, the writhing frequency of each subject of the experimental groups was measured, and for the measurement of the analgesic efficacy, the frequency reduction was calculated as compared to a control group by using Equation 1. The results are shown in Table 3.

Inhibitory effect (%)=[(a control group administered with excipient−a group administered with test material)/a control group administered with excipient]×100    [Equation 1]

TABLE 3

| Compound | Inhibitory effect (%) |
|---|---|
| 29 | 59 (1 hour) |
| 48 | 41 (1 hour) |
| 49 | 49 (2 hour) |
| 50 | 19 (1 hour) |
| 53 | 34 (2 hour) |
| 72 | 31 (0.5 hour) |
| 73 | 39 (1 hour) |

As shown in Table 3, the biaryl benzoimidazole derivative of the invention was found to have an excellent analgesic effect.

Industrial Applicability

The biaryl benzoimidazole derivative of the present invention has an excellent inhibitory effect on calcium influx in HEK cells, thereby showing a powerful antagonistic effect on a vanilloid receptor, and further has an excellent analgesic effect, thereby being useful for preventing or treating pain, acute pain, chronic pain, neuropathic pain, postoperative pain, migraine, arthralgia, neuropathies, nerve injury, diabetic neuropathy, neurological illness, neurodermatitis, stroke, bladder hyper-sensitivity, irritable bowel syndrome, a respiratory disorder such as cough, asthma, and chronic obstructive pulmonary disease, burning, psoriasis, itching, vomiting, irritation of the skin, eyes, and mucous membranes, gastric-duodenal ulcers, inflammatory intestinal diseases, and inflammatory diseases.

The invention claimed is:

1. A biaryl benzoimidazole represented by the following Formula 1, or a pharmaceutically acceptable salt or an isomer thereof, <Formula 1>

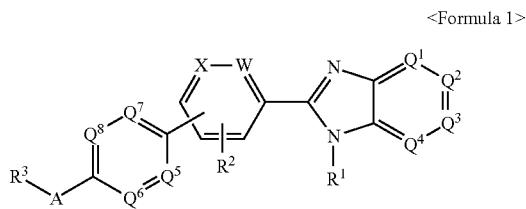

wherein, $R^1$ is hydrogen or $(CR^aR^{a'})_mR^b$;

m is an integer of 0, 1 or 2;

$R^a$ and $R^{a'}$ are each independently hydrogen; halogen; nitro; hydroxy; cyano; azide; amine; $NH(C_{1\sim6}$ alkyl); $N(C_{1\sim6}$ alkyl$)_2$; alkoxy having 1 to 8 carbon atoms; alkyl having 1 to 8 carbon atoms substituted or unsubstituted with one or more $R^c$; alkenyl having 2 to 8 carbon atoms substituted or unsubstituted with one or more $R^c$; phenyl substituted or unsubstituted with one or more $R^c$; or benzyl substituted or unsubstituted with one or more $R^c$;

$R^b$ is hydrogen; hydroxy; alkyl having 1 to 6 carbon atoms substituted or unsubstituted with one or more $R^c$; phenyl substituted or unsubstituted with one or more $R^c$; or benzyl substituted or unsubstituted with one or more $R^c$;

$R^c$ is halogen; cyano; nitro; azide; phenyl; benzyl; $C(=O)R^d$; $C(=O)OR^d$; $C(=O)NR^dR^{d'}$; $OR^d$; $OC(=O)R^e$; $OC(=O)OR^e$; $OC(=O)NR^dR^{d'}$; $OC_{1\sim6}$alkylO$R^d$; $OC_{1\sim6}$alkyNR$^dR^{d'}$; $SR^d$; $S(=O)R^e$; $S(=O)_2R^e$; $S(=O)_2NR^dR^{d'}$; $CR^d=NR^{d'}$; $NR^dR^{d'}$; $NR^dC(=O)R^e$; $NR^dC(=O)OR^e$; $NR^dC(=O)NR^{d'}R^{d''}$; $NR^dC(=NR^{d'})NR^{d''}R^{d'''}$; $NR^dS(=O)_2R^e$; $NR^dOR^{d'}$; $NR^dC_{1\sim6}$alkylNR$^{d'}R^{d''}$; or $NR^dC_{1\sim6}$alkylOR$^{d'}$;

$R^d$, $R^{d'}$, $R^{d''}$ and $R^{d'''}$ are each independently hydrogen or $R^e$;

$R^e$ is phenyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl), and $N(C_{1\sim4}$ alkyl$)_2$; benzyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl), and $N(C_{1\sim4}$ alkyl$)_2$; alkyl having 1 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl), and $N(C_{1\sim4}$ alkyl$)_2$; or phosphoric acid;

$R^2$ is hydrogen; halogen; nitro; hydroxy; cyano; azide; amine; alkoxy having 1 to 8 carbon atoms; haloalkyl having 1 to 6 carbon atoms; haloalkoxy having 1 to 6 carbon atoms; alkyl having 1 to 10 carbon atoms substituted or unsubstituted with one or more $R^f$; alkenyl having 2 to 10 carbon atoms substituted or unsubstituted with one or more $R^f$; alkynyl having 2 to 10 carbon atoms substituted or unsubstituted with one or more $R^f$; cycloalkyl having 3 to 10 carbon atoms substituted or unsubstituted with one or more $R^f$; bicycloalkyl having 8 to 14 carbon atoms substituted or unsubstituted with one or more $R^f$; cycloalkenyl having 3 to 10 carbon atoms substituted or unsubstituted with one or more $R^f$; bicycloalkenyl having 8 to 14 carbon atoms substituted or unsubstituted with one or more $R^f$; phenyl substituted or unsubstituted with one or more $R^f$; naphthyl substituted or unsubstituted with one or more $R^f$; benzyl substituted or unsubstituted with one or more $R^f$; $C(=O)R^d$; $C(=O)OR^d$; $C(=O)NR^dR^{d'}$; $OR^d$; $OC(=O)R^e$; $OC(=O)OR^e$; $OC(=O)NR^dR^{d'}$; $OC_{1\sim6}$alkylOR$^d$; $OC_{1\sim6}$alkylNR$^dR^{d'}$; $SR^d$; $S(=O)R^e$; $S(=O)_2R^e$; $S(=O)_2NR^dR^{d'}$; $CR^d=NR^{d'}$; $NR^dR^{d'}$; $NR^dC(=O)R^e$; $NR^dC(=O)OR^e$; $NR^dC(=O)NR^{d'}R^{d''}$; $NR^dC(=NR^{d'})NR^{d''}R^{d'''}$ $NR^{d''}R^{d'''}$; $NR^dS(=O)_2R^e$; $NR^dOR^{d'}$; $NR^dC_{1\sim6}$alkylNR$^{d'}R^{d''}$; or $NR^dC_{1\sim6}$alkylOR$^{d'}$;

$R^f$ is alkyl having 1 to 6 carbon atoms; alkenyl having 2 to 6 carbon atoms; alkynyl having 2 to 6 carbon atoms; haloalkyl having 1 to 6 carbon atoms; haloalkoxy having 1 to 6 carbon atoms; halogen; azide; nitro; cyano; phenyl; benzyl; $C(=O)R^d$; $C(=O)OR^d$; $C(=O)NR^dR^{d'}$; $OR^d$; $OC(=O)R^e$; $OC(=O)OR^e$; $OC(=O)NR^dR^{d'}$; $OC_{1\sim6}$alkylOR$^d$; $OC_{1\sim6}$alkylNR$^dR^{d'}$; $SR^d$; $S(=O)R^e$; $S(=O)_2R^e$; $S(=O)_2NR^dR^{d'}$; $CR^d=NR^{d'}$; $NR^dR^{d'}$; $NR^dC(=O)R^e$; $NR^dC(=O)OR^e$; $NR^dC(=O)NR^{d'}R^{d''}$; $NR^dC(=NR^{d'})NR^{d''}R^{d'''}$; $NR^dS(=O)_2R^e$; $NR^dOR^{d'}$; $NR^dC_{1\sim6}$alkylNR$^{d'}R^{d''}$; or $NR^dC_{1\sim6}$alkylOR$^{d'}$;

A is $(CR^gR^{g'})_pZ$ or $Z(CR^gR^{g'})_p$;

p is an integer of 0, 1 or 2;

Z is $C(=O)$; $C(=O)O$; $C(=O)NR^d$; $C(=NR^d)$; $C(=NR^d)NR^{d'}$; $C(=O)C_{1\sim6}$alkylC$(=O)$; $C(=O)C_{1\sim6}$alkylO; $C(=O)C_{1\sim6}$alkylS; $C(=O)C_{1\sim6}$alkylS$(=O)_2$; $C(=O)C_{1\sim6}$alkylNR$^d$; O; $OC(=O)$; $OC(=O)NR^d$; $OC(=O)NR^dS(=O)_2$; $OC_{1\sim6}$alkylC$(=O)$; $OC_{1\sim6}$alkylO; $OC_{1\sim6}$alkylS; $OC_{1\sim6}$alkylS$(=O)_2$; $OC_{1\sim6}$alkylNR$^d$; S; $SC_{1\sim6}$alkylC$(=O)$; $SC_{1\sim6}$alkylO; $SC_{1\sim6}$alkylS; $SC_{1\sim6}$alkylS$(=O)_2$; $SC_{1\sim6}$alkylNR$^d$; $S(=O)$; $S(=O)_2$; $S(=O)_2NR^d$; $S(=O)_2NR^dC(=O)$; $S(=O)_2NR^dC(=O)O$; $S(=O)_2NR^dC(=O)NR^{d'}$; $S(=O)_2C_{1\sim6}$alkylC$(=O)$; $S(=O)_2C_{1\sim6}$alkylO; $S(=O)_2C_{1\sim6}$alkylS; $S(=O)_2C_{1\sim6}$alkylS$(=O)_2$; $S(=O)_2C_{1\sim6}$alkylNR$^d$; $NR^d$; $NR^dC(=O)$; $NR^dC(=O)O$; $NR^dC(=O)NR^{d'}$; $NR^dC(=NR^{d'})NR^{d''}$; $NR^dS(=O)_2$; $NR^dS(=O)_2NR^{d'}$; $NR^dC_{1\sim6}$alkylC$(=O)$; $NR^dC_{1\sim6}$alkylO; $NR^dC_{1\sim6}$alkylS; $NR^dC_{1\sim6}$alkylS$(=O)_2$; or $NR^dC_{1\sim6}$alkylNR$^{d'}$;

$R^g$ and $R^{g'}$ are each independently hydrogen; halogen; nitro; hydroxy; cyano; azide; amine; $NH(C_{1\sim6}$ alkyl); $N(C_{1\sim6}$ alkyl$)_2$; alkoxy having 1 to 8 carbon atoms; alkyl having 1 to 8 carbon atoms substituted or unsubstituted with one or more $R^c$; alkenyl having 2 to 8 carbon atoms substituted or unsubstituted with one or more $R^c$; phenyl substituted or unsubstituted with one or more $R^c$; or benzyl substituted or unsubstituted with one or more $R^c$;

$R^3$ is hydrogen; halogen; nitro; hydroxy; cyano; azide; amine; alkoxy having 1 to 8 carbon atoms; haloalkyl having 1 to 6 carbon atoms; haloalkoxy having 1 to 6 carbon atom; alkyl having 1 to 10 carbon atoms substituted or unsubstituted with one or more $R^f$; alkenyl having 2 to 10 carbon atoms substituted or unsubstituted with one or more $R^f$; alkynyl having 2 to 10 carbon atoms substituted or unsubstituted with one or more $R^f$; cycloalkyl having 3 to 10 carbon atoms substituted or unsubstituted with one or more $R^f$; bicycloalkyl having 8 to 14 carbon atoms substituted or unsubstituted with one or more $R^f$; cycloalkenyl having 3 to 10 carbon atoms substituted or unsubstituted with one or more $R^f$; bicycloalkenyl having 8 to 14 carbon atoms substituted or unsubstituted with one or more $R^f$; phenyl substituted or unsubstituted with one or more $R^f$; naphthyl substituted or unsubstituted with one or more $R^f$; or benzyl substituted or unsubstituted with one or more $R^f$;

$Q^1$ is $CR^4$;
$Q^2$ is $CR^5$;
$Q^3$ is $CR^{5'}$;
$Q^4$ is $CR^{4'}$;
$Q^5$ is N;
$Q^6$ is $CR^7$;
$Q^7$ is $CR^{6'}$;
$Q^8$ is $CR^{7'}$;
W is N;
X is $CR^{8'}$;

$R^4$, $R^{4'}$, $R^5$, $R^{5'}$, $R^6$, $R^{6'}$, $R^7$ and $R^{7'}$ are the same or different from each other, and each independently hydrogen; halogen; nitro; hydroxy; cyano; azide; amine; alkoxy having 1 to 8 carbon atoms; haloalkyl having 1 to 6 carbon atoms; haloalkoxy having 1 to 6 carbon atoms; alkyl having 1 to 10 carbon atoms substituted or unsubstituted with one or more $R^h$; alkenyl having 2 to 10 carbon atoms substituted or unsubstituted with one or more $R^h$; alkynyl having 2 to 10 carbon atoms substituted or unsubstituted with one or more $R^h$; cycloalkyl having 3 to 10 carbon atoms substituted or unsubstituted with one or more $R^h$; bicycloalkyl having 8 to 14 carbon atoms substituted or unsubstituted with one or more $R^h$; cycloalkenyl having 3 to 10 carbon atoms substituted or unsubstituted with one or more $R^h$; bicycloalkenyl having 8 to 14 carbon atoms substituted or unsubstituted with one or more $R^h$; phenyl substituted or unsubstituted with one or more $R^h$; naphthyl substituted or unsubstituted with one or more $R^h$; benzyl substituted or unsubstituted with one or more $R^h$; $C(=O)R^i$; $C(=O)OR^i$; $C(=O)NR^iR^{i'}$; $OR^i$; $OC(=O)R^j$; $OC(=O)OR^j$; $OC(=O)NR^iR^i$; $OC_{1\sim6}$alkyl$OR^i$; $OC_{1\sim6}$alkyl$NR^iR^{i'}$; $SR^i$; $S(=O)R^j$; $S(=O)_2R^j$; $S(=O)_2NR^iR^{i'}$; $CR^i=NR^{i'}$; $NR^iR^{i'}$; $NR^iC(=O)R^j$; $NR^iC(=O)OR^j$; $NR^iC(=O)NR^iR^{i''}$; $NR^iC(=NR^{i'})NR^{i''}R^{i'''}$; $NR^iS(=O)_2R^j$; $NR^iOR^{i'}$; $NR^iC_{1\sim6}$alkyl$NR^{i'};R^{i''}$; $NR^iC_{1\sim6}$alkyl$OR^i$;

$R^h$ is alkyl having 1 to 6 carbon atoms; alkenyl having 2 to 6 carbon atoms; alkynyl having 2 to 6 carbon atoms; cycloalkyl having 3 to 8 carbon atoms; cycloalkenyl having 5 to 8 carbon atoms; haloalkyl having 1 to 6 carbon atoms; haloalkoxy having 1 to 6 carbon atoms; halogen; azide; nitro; cyano; phenyl; benzyl; $C(=O)R^i$; $C(=O)OR^i$; $C(=O)NR^iR^{i'}$; $OR^i$; $OC(=O)R^j$; $OC(=O)OR^j$; $OC(=O)NR^iR^i$; $OC_{1\sim6}$alkyl$OR^i$; $OC_{1\sim6}$alkyl$NR^iR^{i'}$; $SR^i$; $S(=O)R^j$; $S(=O)_2R^j$; $S(=O)_2NR^iR^{i'}$; $CR^i=NR^{i'}$; $NR^iR^{i'}$; $NR^iC(=O)R^j$; $NR^iC(=O)OR^j$; $NR^dC(=O)NR^iR^i$; $NR^iC(=NR^{i'})NR^{i''}R^{i'''}$; $NR^iS(=O)_2R^j$; $NR^iOR^{i'}$; $NR^iC_{1\sim6}$alkyl$NR^{i'}R^{i''}$; $NR^iC_{1\sim6}$alkyl $OR^i$;

$R^i$, $R^{i'}$, $R^{i''}$ and $R^{i'''}$ are each independently hydrogen or $R^j$;
$R^j$ is phenyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl) and $N(C_{1\sim4}$ alkyl$)_2$;
benzyl substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl) and $N(C_{1\sim4}$ alkyl$)_2$;

alkyl having 1 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl) and $N(C_{1\sim4}$ alkyl$)_2$;

alkenyl having 2 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl) and $N(C_{1,4}$ alkyl$)_2$;

alkynyl having 2 to 6 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl) and $N(C_{1\sim4}$ alkyl$)_2$;

cycloalkyl having 3 to 8 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl) and $N(C_{1\sim4}$ alkyl$)_2$;

cycloalkenyl having 5 to 8 carbon atoms substituted or unsubstituted with one or more groups selected from the group consisting of hydroxy, halogen, alkyl having 1 to 4 carbon atoms, haloalkyl having 1 to 3 carbon atoms, alkoxy having 1 to 4 carbon atoms, amine, $NH(C_{1\sim4}$ alkyl) and $N(C_{1\sim4}$ alkyl$)_2$;

$R^8$ and $R^{8'}$ are the same or different from each other, and each independently hydrogen; halogen; nitro; hydroxy; cyano; azide; amine; alkoxy having 1 to 8 carbon atoms; haloalkyl having 1 to 6 carbon atoms; haloalkoxy having 1 to 6 carbon atoms; alkyl having 1 to 10 carbon atoms substituted or unsubstituted with one or more $R^h$; alkenyl having 2 to 10 carbon atoms substituted or unsubstituted with one or more $R^h$; alkynyl having 2 to 10 carbon atoms substituted or unsubstituted with one or more $R^h$; cycloalkyl having 3 to 10 carbon atoms substituted or unsubstituted with one or more $R^h$; bicycloalkyl having 8 to 14 carbon atoms substituted or unsubstituted with one or more $R^h$; cycloalkenyl having 3 to 10 carbon atoms substituted or unsubstituted with one or more $R^h$; bicycloalkenyl having 8 to 14 carbon atoms substituted or unsubstituted with one or more $R^h$; phenyl substituted or unsubstituted with one or more $R^h$; naphthyl substituted or unsubstituted with one or more $R^h$; benzyl substituted or unsubstituted with one or more $R^h$; $C(=O)R^i$; $C(=O)OR^i$; $C(=O)NR^iR^{i'}$; $OR^i$; $OC(=O)R^j$; $OC(=O)OR^j$; $OC(=O)NR^iR^{i'}$; $OC_{1\sim6}$alkyl$OR^i$; $OC_{1\sim6}$alkyl$NR^iR^{i'}$; $SR^i$; $S(=O)R^j$; $S(=O)_2R^j$; $S(=O)_2NR^iR^{i'}$; $CR^i=NR^{i'}$; $NR^iR^{i'}$; $NR^iC(=O)R^j$; $NR^iC(=O)OR^j$; $NR^iC(=O)NR^iR^{i''}$; $NR^iC(=NR^{i'})NR^{i''}R^{i'''}$; $NR^iS(=O)_2R^j$; $NR^iOR^{i'}$; $NR^iC_{1\sim6}$alkyl$NR^{i'Ri''}$; $NR^iC_{1\sim6}$alkyl$OR^i$.

2. The biaryl benzoimidazole represented by the following Formula 1, or a pharmaceutically acceptable salt or an isomer thereof according to claim 1, wherein the compound of Formula 1 is selected from the group consisting of 1) 3-chloro-6'-(6-trifluoromethyl-1H-benzoimidazol-2-yl)-[2,3']bipyridinyl-5-carboxylic acid methyl ester,
2) 6'-(6-tert-butyl-1H-benzoimidazol-2-yl)-3-chloro-[2,3'] bipyridinyl-5-carboxylic acid methyl ester, 3) 6'-(6-bromo-1H-benzoimidazol-2-yl)-3-chloro-[2,3']bipyridinyl-5-carboxylic acid methyl ester,
4) 6'-(4-bromo-6-trifluoromethyl-1H-benzoimidazol-2-yl)-3-chloro-[2,3']bipyridinyl-5-carboxylic acid methyl ester,
5) 3-chloro-6'-(4,6-dibromo-1H-benzoimidazol-2-yl)-[2,3']bipyridinyl-5-carboxylic acid methyl ester,
6) 3-chloro-6'-(6-trifluoromethyl-1H-benzoimidazol-2-yl)-[2,3']bipyridinyl-5-carboxylic acid,
7) 6'-(6-tert-butyl-1H-benzoimidazol-2-yl)-3-chloro-[2,3']bipyridinyl-5-carboxylic acid,
8) 6'-(6-bromo-1H-benzoimidazol-2-yl)-3-chloro-[2,3']bipyridinyl-5-carboxylic acid,
9) 6'-(4-bromo-6-trifluoromethyl-1H-benzoimidazol-2-yl)-3-chloro-[2,3']bipyridinyl-5-carboxylic acid,
10) 3-chloro-6'-(4,6-dibromo-1H-benzoimidazol-2-yl)-[2,3']bipyridinyl-5-carboxylic acid,
11) [3-chloro-6'-(6-trifluoromethyl-1H-benzoimidazol-2-yl)-[2,3']bipyridinyl-5-yl]-methanol,
12) [6'-(6-tert-butyl-1H-benzoimidazol-2-yl)-3-chloro-[2,3']bipyridinyl-5-yl]-methanol,
13) [6'-(6-bromo-1H-benzoimidazol-2-yl)-3-chloro-[2,3']bipyridinyl-5-yl]-methanol,
14) [6'-(4-bromo-6-trifluoromethyl-1H-benzoimidazol-2-yl)-3-chloro-[2,3']bipyridinyl-5-yl]-methanol,
15) [3-chloro-6'-(4,6-dibromo-1H-benzoimidazol-2-yl)-[2,3']bipyridinyl-5-yl]-methanol,
16) 3-chloro-6'-(6-trifluoromethyl-1H-benzoimidazol-2-yl)-[2,3']bipyridinyl-5-carboxylic acid ethyl amide,
17) 6'-(6-tert-butyl-1H-benzoimidazol-2-yl)-3-chloro-[2,3']bipyridinyl-5-carboxylic acid ethyl amide,
18) 6'-(6-bromo-1H-benzoimidazol-2-yl)-3-chloro-[2,3']bipyridinyl-5-carboxylic acid ethyl amide,
19) 6'-(6-bromo-1H-imidazo[4,5-b]pyridin-2-yl)-3-chloro-[2,3']bipyridinyl-5-carboxylic acid ethyl amide,
20) 6'-(4-bromo-6-trifluoromethyl-1H-benzoimidazol-2-yl)-3-chloro-[2,3']bipyridinyl-5-carboxylic acid ethyl amide,
21) 3-chloro-6'-(4,6-dibromo-1H-benzoimidazol-2-yl)-[2,3']bipyridinyl-5-carboxylic acid ethyl amide,
22) 6'-(6-tert-butyl-1H-benzoimidazol-2-yl)-3-chloro-5-vinyl-[2,3']bipyridinyl,
23) 3-chloro-6'-(6-trifluoromethyl-1H-benzoimidazol-2-yl)-5-vinyl-[2,3']bipyridinyl,
24) 6'-(6-bromo-1H-benzoimidazol-2-yl)-3-chloro-5-vinyl-[2,3']bipyridinyl,
25) 3-chloro-6'-(6-chloro-1H-benzoimidazol-2-yl)-5-vinyl-[2,3']bipyridinyl, and
26) 6'-(4-bromo-6-trifluoromethyl-1H-benzoimidazol-2-yl)-3-chloro-5-vinyl-[2,3']bipyridinyl.

3. A pharmaceutical composition comprising the biaryl benzoimidazole, or a pharmaceutically acceptable salt or an isomer thereof of claim 1 and an inert carrier.

4. A method for treating a disease selected from the group consisting of pain, acute pain, chronic pain, neuropathic pain, postoperative pain, migraine, arthralgia, diabetic neuropathy, bladder hypersensitivity, cough, asthma, chronic obstructive pulmonary disease, psoriasis, itching, irritation of the skin, eyes, and mucous membranes, comprising a step of administering a therapeutically effective amount of the biaryl benzoimidazole, or a pharmaceutically acceptable salt or an isomer thereof of claim 1 to a mammal in need thereof.

5. A pharmaceutical composition comprising the biaryl benzoimidazole, or a pharmaceutically acceptable salt or an isomer thereof of claim 2; and an inert carrier.

6. A method for treating a disease selected from the group consisting of pain, acute pain, chronic pain, neuropathic pain, postoperative pain, migraine, arthralgia, diabetic neuropathy, bladder hypersensitivity, cough, asthma, chronic obstructive pulmonary disease, psoriasis, itching, irritation of the skin, eyes, and mucous membranes, comprising a step of administering a therapeutically effective amount of the biaryl benzoimidazole, or a pharmaceutically acceptable salt or an isomer thereof of claim 2 to a mammal in need thereof.

* * * * *

UNITED STATES PATENT AND TRADEMARK OFFICE
CERTIFICATE OF CORRECTION

PATENT NO. : 8,436,022 B2  Page 1 of 1
APPLICATION NO. : 12/373193
DATED : May 7, 2013
INVENTOR(S) : Kim et al.

It is certified that error appears in the above-identified patent and that said Letters Patent is hereby corrected as shown below:

On the Title Page, Item [54] and in the Specification, Column 1, Title, should read:

BIARYL ~~BENZOLMIDAZOLE~~ BENZOIMIDAZOLE DERIVATIVES
AND PHARMACEUTICAL COMPOSITION COMPRISING THE SAME

Signed and Sealed this
Twenty-fifth Day of February, 2014

Michelle K. Lee
*Deputy Director of the United States Patent and Trademark Office*